US011020590B2

(12) United States Patent
Pakhomov et al.

(10) Patent No.: US 11,020,590 B2
(45) Date of Patent: Jun. 1, 2021

(54) TARGETED REMOTE ELECTROSTIMULATION BY INTERFERENCE OF BIPOLAR NANOSECOND PULSES

(71) Applicant: Old Dominion University Research Foundation, Norfolk, VA (US)

(72) Inventors: Andrei G. Pakhomov, Norfolk, VA (US); Olga N. Pakhomova, Norfolk, VA (US); Shu Xiao, Norfolk, VA (US)

(73) Assignee: OLD DOMINION UNIVERSITY RESEARCH FOUNDATION, Norfolk, VA (US)

(*) Notice: Subject to any disclaimer, the term of this patent is extended or adjusted under 35 U.S.C. 154(b) by 344 days.

(21) Appl. No.: 16/104,089

(22) Filed: Aug. 16, 2018

(65) Prior Publication Data
US 2019/0054294 A1    Feb. 21, 2019

Related U.S. Application Data

(60) Provisional application No. 62/546,229, filed on Aug. 16, 2017.

(51) Int. Cl.
| A61N 1/32 | (2006.01) |
| A61N 1/36 | (2006.01) |
| A61N 1/04 | (2006.01) |
| C12N 13/00 | (2006.01) |

(52) U.S. Cl.
CPC ............ *A61N 1/323* (2013.01); *A61N 1/327* (2013.01); *C12N 13/00* (2013.01); *A61N 1/0412* (2013.01); *A61N 1/0476* (2013.01); *A61N 1/36* (2013.01)

(58) Field of Classification Search
CPC ..................................................... A61N 1/323
See application file for complete search history.

(56) References Cited

U.S. PATENT DOCUMENTS

| 2008/0228244 A1* | 9/2008 | Pakhomov ......... A61N 1/36034 607/72 |
| 2010/0261994 A1 | 10/2010 | Davalos et al. |
| 2014/0194949 A1* | 7/2014 | Wichner ............... A61N 1/323 607/48 |

OTHER PUBLICATIONS

Semenov, I., Xiao, S. & Pakhomov, A.G. Primary pathways of intracellular Ca{2+) mobilization by nanosecond pulsed electric field. Biochim Biophys Acta 1828, 981-9 (2013).
Semenov, Recruitment of the intracellular Ca2+ by ultrashort electric stimuli: the impact of pulse duration., Cell Calcium, 2013, 54(3):145-150.
Tarek, Membrane electroporation: a molecular dynamics simulation., Biophysical journal, 2005, 88(6):4045-4053.
Teissie, Electropermeabilization of cell membranes., Advanced drug delivery reviews, 1999, 35(1):3-19.

(Continued)

*Primary Examiner* — Michael W Kahelin
(74) *Attorney, Agent, or Firm* — MH2 Technology Law Group, LLP

(57) ABSTRACT

Provided herein are methods of generating a biologically effective unipolar nanosecond electric pulse by superposing two biologically ineffective bipolar nanosecond electric pulses and related aspects, such as electroporation and/or therapeutic applications of these methods to non-invasively target electrostimulation (ES) selectively to deep tissues and organs.

32 Claims, 15 Drawing Sheets

(56) References Cited

OTHER PUBLICATIONS

Tekle, Electroporation by using bipolar oscillating electric field: an improved method for DNA transfection of NIH 3T3 cells., Proceedings of the National Academy of Sciences of the United States of America, 1991, 88(10):4230-4234.
Thompson, G.L. et al. Permeabilization of the nuclear envelope following nanosecond pulsed electric field exposure. Biochem Biophys Res Commun 470, 35-40 (2016).
Tolstykh, 600 ns pulse electric field-induced phosphatidylinositol4,5-bisphosphate depletion., Bioelectrochemistry, 2014, 100:80-87.
Tsong, Electroporation of cell membranes., Biophysical journal, 1991, 60(2):297-306.
Ullery, Activation of autophagy in response to nanosecond pulsed electric field exposure., Biochemical and biophysical research communications, 2015, 458(2):411-417.
Valdez, Asymmetrical bipolar nanosecond electric pulse widths modify bipolar cancellation., Scientific reports, 2017, 7(1):16372.
Vernier, Nanosecond electric pulse-induced calcium entry into chromaffin cells., Bioelectrochemistry, 2008, 73(1):1-4.
Vernier, P.T., Sun, Y., Marcu, L., Craft, C.M. & Gundersen, M.A. Nanoelectropulse-induced phosphatidylserine translocation. Biophys J 86, 4040-8 (2004).
International Preliminary Report on Patentability issued in corresponding International Application No. PCT/US2018/046823 dated Feb. 25, 2020, pp. 1-65.
Batista Napotnik, Effects of high voltage nanosecond electric pulses on eukaryotic cells (in vitro): A systematic review., Bioelectrochemistry, 2016, 110:1-12.
Batista Napotnik, Nanosecond electric pulses cause mitochondrial membrane permeabilization in Jurkat cells., Bioelectromagnetics, 2012, 33(3):257-264.
Beebe, S.J., Fox, P.M., Rec, L.J., Willis, E.L. & Schoenbach, K.H. Nanosecond, high-intensity pulsed electric fields induce apoptosis in human cells. Faseb J 17, 1493-5 (2003).
Beebe, Transient features in nanosecond pulsed electric fields differentially modulate mitochondria and viability., PLoS One, 2012, 7(12):e51349.
Chemeris, Lack of direct DNA damage in human blood leukocytes and lymphocytes after in vitro exposure to high power microwave pulses., Bioelectromagnetics, 2006, 27(3):197-203.
Cobb, Neural and behavioral teratological evaluation of rats exposed to ultra-wideband electromagnetic fields., Bioelectromagnetics, 2000, 21(7):524-537.
Craviso, Modulation of intracellular Ca2+ levels in chromaffin cells by nanoelectropulses., Bioelectrochemistry, 2012, 87:244-252.
Davalos, Tissue ablation with irreversible electroporation., Annals of biomedical engineering, 2005, 33(2):223-231.
Dmochowski, Noninvasive Neuromodulation Goes Deep., Cell, 2017, 169(6):977-978.
Frandsen, Direct therapeutic applications of calcium electroporation to effectively induce tumor necrosis., Cancer Res, 2012, 72(6):1336-1341.
Gianulis, Electropermeabilization by uni- or bipolar nanosecond electric pulses: The impact of extracellular conductivity., Bioelectrochemistry, 2018, 119:10-19.
Gianulis, Electroporation of mammalian cells by nanosecond electric field oscillations and its inhibition by the electric field reversal., Scientific reports, 2015.
Grossman, Noninvasive Deep Brain Stimulation via Temporally Interfering Electric Fields., Cell, 2017, 169(6):1029-1041 e1016.
Ho, Molecular dynamics simulations of ion conductance in field-stabilized nanoscale lipid electropores., The journal of physical chemistry, 2013, B.
Ibey, Bipolar nanosecond electric pulses are less efficient at electropermeabilization and killing cells than monopolar pulses., Biochemical and biophysical research communications, 2014, 443(2):568-573.
Ibey, Cellular effects of acute exposure to high peak power microwave systems: Morphology and toxicology., Bioelectromagnetics, 2016.
Jauchem, Ultra-wideband electromagnetic pulses: lack of effects on heart rate and blood pressure during two-minute exposures of rats., Bioelectromagnetics, 1998, 19(5):330-333.
Kotnik, Cell membrane electropermeabilization by symmetrical bipolar rectangular pulses. Part I. Reduced electrolytic contamination., Bioelectrochemistry, 2001, 54(1):91-95.
Kotnik, Cell membrane electropermeabilization by symmetrical bipolar rectangular pulses. Part II. Reduced electrolytic contamination., Bioelectrochemistry, 2001, 54(1):83-90.
Kotnik, Role of pulse shape in cell membrane electropermeabilization., Biochimica et biophysica acta, 2003, 1614(2):193-200.
Lin, Hearing of microwave pulses by humans and animals: effects, mechanism, and thresholds., Health physics, 2007, 92(6):621-628.
Lu, Effects of high peak power microwaves on the retina of the rhesus monkey., Bioelectromagnetics, 2000, 21(6):439-454.
Merla, Frequency spectrum of induced transmembrane potential and permeabilization efficacy of bipolar electric pulses., Biochimica et biophysica acta, 2017, 1859(7)1282-1290.
Miklavcic, Electrochemotherapy (ECT) and irreversible electroporation (IRE)-advanced techniques for treating deep-seated tumors based on electroporation., Biomedical engineering online, 2015, 14 Suppl 3:11.
Miklavcic, Electrochemotherapy: from the drawing board into medical practice., Biomedical engineering online, 2014, 13(1):29.
Morotomi-Yano, Different involvement of extracellular calcium in two modes of cell death induced by nanosecond pulsed electric fields., Arch Biochem Biophys, 2014.
Muratori, Electrosensitization assists cell ablation by nanosecond pulsed electric field in 3D cultures., Scientific reports, 2016, 6:23225.
Neumann, Membrane electroporation and direct gene transfer., Bioelectrochemistry and Bioenergetics, 1992, 28(1):247-267.
Nizard, Non-invasive stimulation therapies for the treatment of refractory pain., Discovery medicine, 2012, 14 (74)21-31.
Pakhomov, A.G. et al. Lipid nanopores can form a stable, ion channel-like conduction pathway in cell membrane. Biochem Biophys Res Commun 385, 181-6 (2009).
Pakhomov, Advanced Electroporation Techniques in Biology and Medicine, 2010, (CRC Press, Boca Raton), p. 528.
Pakhomov, Cancellation of cellular responses to nanoelectroporation by reversing the stimulus polarity., Cellular and molecular life sciences, 2014, 71(22):4431-4441.
Pakhomov, Comparative effects of extremely high power microwave pulses and a brief CW irradiation on pacemaker function in isolated frog heart slices., Bioelectromagnetics, 2000, 21(4):245-254.
Pakhomov, Comparison of dose dependences for bioeffects of continuous-wave and high-peak power microwave emissions using gel-suspended cell cultures., Bioelectromagnetics, 2002, 23(2):158-167.
Pakhomov, Current state and implications of research on biological effects of millimeter waves: a review of the literature., Bioelectromagnetics, 1998, 19(7):393-413.
Pakhomov, Disassembly of actin structures by nanosecond pulsed electric field is a downstream effect of cell swelling., Bioelectrochemistry, 2014, 100:88-95.
Pakhomov, Effects of high power microwave pulses on synaptic transmission and long term potentiation in hippocampus., Bioelectromagnetics, 2003, 24(3):174-181.
Pakhomov, Long-lasting plasma membrane permeabilization in mammalian cells by nanosecond pulsed electric field (nsPEF)., Bioelectromagnetics, 2007, 28, 655-663.
Pakhomov, Multiple nanosecond electric pulses increase the number but not the size of long-lived nanopores in the cell membrane., Biochimica et biophysica acta, 2015, 1848(4):958-966.
Pakhomov, The second phase of bipolar, nanosecond-range electric pulses determines the electroporation efficiency., Bioelectrochemistry, 2018, 122:123-133.
Pakhomov, Two modes of cell death caused by exposure to nanosecond pulsed electric field., PLoS One, 2013, 8(7):e70278.

(56) References Cited

OTHER PUBLICATIONS

Pakhomov, Ultra-wide band electromagnetic radiation does not affect UV-induced recombination and mutagenesis in yeast., Bioelectromagnetics, 1998, 19(2):128-130.
Ren, W., Sain, N. M. & Beebe, S.J. Nanosecond pulsed electric fields {nsPEFs) activate intrinsic caspase-dependent and caspase-independent cell death in Jurkat cells. Biochemical and biophysical research communications 421, 808-12 (2012).
Roth, Three-dimensional distribution of the electric field induced in the brain by transcranial magnetic stimulation using figure-8 and deep H-coils., Journal of clinical neurophysiology: official publication of the American Electroencephalographic Society, 2007, 24(1):31-38.
Ryan, High-Voltage, Multiphasic, Nanosecond Pulses to Modulate Cellular Responses. , IEEE Transactions on Biomedical Circuits and Systems, 2018, (99):1-13.
Schoenbach, Ion transport into cells exposed to monopolar and bipolar nanosecond pulses., Bioelectrochemistry, 2015, 103:44-51.
Schoenbach, K.S. et al. Bioelectric Effects of Intense Nanosecond Pulses. IEEE Transactions on Dielectrics and Electrical Insulation 14, 1088-1109 (2007).
Schunck, Penetration and propagation into biological matter and biological effects of high-power ultra-wideband pulses: a review., Electromagnetic biology and medicine, 2016, 35(1):84-101.
Seaman, Effects of exposure of animals to ultra-wideband pulses., Health physics, 2007, 92(6):629-634.
Semenov, Electropermeabilization of cells by closely spaced paired nanosecond-range pulses., Bioelectrochemistry, 2018, 121:135-141.

\* cited by examiner

TARGETED REMOTE ELECTROSTIMULATION BY INTERFERENCE OF BIPOLAR NANOSECOND PULSES

CROSS REFERENCE TO RELATED APPLICATIONS

This application claims the benefit of, and relies on the filing date of, U.S. Provisional Patent Application No. 62/546,229, filed Aug. 16, 2017, the entire disclosure of which is incorporated by reference.

GOVERNMENT SUPPORT

This invention was made with government support under FA9550-15-1-0517 awarded by Air Force Office of Scientific Research. The government has certain rights in the invention.

BACKGROUND

Electrostimulation (ES) is used to manipulate biological function in various applications. Nonetheless, there remains a need in the art, for example, to non-invasively target ES selectively to deep tissues and organs.

SUMMARY

In one aspect, this disclosure provides a method of generating a biologically effective unipolar nanosecond electric pulse. The method includes superposing a first biologically ineffective bipolar nanosecond electric pulse generated from a first pair of electrodes and a second biologically ineffective bipolar nanosecond electric pulse generated from a second pair of electrodes to create the biologically effective unipolar nanosecond electric pulse at a location remote from the first and second pair of electrodes. The biologically effective unipolar nanosecond electric pulse has an enhanced stimulus efficiency as compared to the first or second biologically ineffective bipolar nanosecond electric pulse generated in the absence of the superposing step. The first or second biologically ineffective bipolar nanosecond electric pulse generated in the absence of the superposing step induces a cancellation effect caused by a second phase of the first or second biologically ineffective bipolar nanosecond electric pulse cancelling or reducing a stimulatory effect of a first phase of the first or second biologically ineffective bipolar nanosecond electric pulse. In addition, the enhanced stimulus efficiency of the biologically effective unipolar nanosecond electric pulse is caused by cancelling or reducing the cancellation effect.

In some embodiments, the first and second pair of electrodes is each connected to an independent nanosecond electric pulse-delivering channel. In certain embodiments, the first and second pair of electrodes is each aligned in a linear array. In some embodiments, the unipolar nanosecond electric pulse is non-invasively delivered to a subject. Optionally, the unipolar nanosecond electric pulse is non-invasively delivered to a localized cell, tissue or organ in the subject. In certain embodiments, the unipolar nanosecond electric pulse is non-invasively delivered to a localized cell, tissue or organ in the subject. In some embodiments, the unipolar tissue is a deep tissue. In other embodiments, the unipolar nanosecond electric pulse is delivered to a sample, typically in vitro or ex vivo. Optionally, the sample contains cells. In some embodiments, the enhanced stimulus efficiency of the biologically effective unipolar nanosecond electric pulse is directionally proportional to the extent of cancellation or reduction of the cancellation effect. In certain embodiments, the first and/or second biologically ineffective bipolar nanosecond electric pulses are biphasic or triphasic. In some embodiments, the first and/or second biologically ineffective bipolar nanosecond electric pulses have at least a first and second phase and the amplitude of the first phase is 100/70/40%.

Another aspect is directed to an apparatus for carrying out the methods described herein. Yet another aspect is directed to the use of such an apparatus for treating a subject in need of electroporation. In certain embodiments, the apparatus is used in a therapeutic application, including, but not limited to, pain control, nerve or muscle excitation, activation of immune or endocrine cells, targeted ablation of tumors, treatment of psychiatric disorders, or treatment of Parkinson's disease. The apparatus may also be used in non-therapeutic applications, including, for example, electroporation.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 6A) Schematic showing the nsEP delivered from each pair of electrodes in the 4-electrode linear array. Channel 1 electrodes (1 and 2) delivered a biphasic nsEP (bi-AB), and Channel 2 electrodes (3 and 4) delivered a uniphasic pulse (uni-C). The amplitude of uni-C was the same as that of the second phase of bi-AB, and was 50% of the first phase (set as 100%). A "CANCAN" exposure is considered when uni-C is phase-shifted and synchronized with bi-AB delivery. Alternatively, when the two nsEP are delivered 10-ms apart, the exposure is considered to be "asynchronized." The arrow between 2a and 3a indicates the region where measurements were taken. FIG. 6B) Representative bright field (BF, top panels) or fluorescent (YP, bottom panels) images encompassing the middle pair of electrodes (2 and 3) for each exposure condition. Scale bar=500 µm. In each image, the left and right circles correspond to the imprints of electrodes 2 and 3, respectively. YP uptake was quantified within 16 regions of interest drawn along the X-axis between the electrodes (white dashed line on the left side of YP panel in FIG. 6B), and plotted as a function of the local electric field during uni-A as seen in FIG. 6C). (FIG. 6D) shows the ratio of the "CANCAN" exposure to the "asynchronized" exposure as a function of distance between electrodes 2 and 3. Mean±S.E., n=5.

FIG. 7A) Channel 1 electrodes (2 and 3) delivered a triphasic bipolar nsEP (bi-ABC) and Channel 2 electrodes (3 and 4) delivered a biphasic nsEP (bi-DE). The amplitudes of the second and third phases (B/D and C/E, respectively) were adjusted in each set of experiments to be either 50% and 25% (FIGS. 7B & C), 70% and 25% (FIGS. 7D & E), or 70% and 40% (FIGS. 7F & G) of the first phase, respectively (set as 100%). YP uptake was quantified along the X-axis between electrodes 2 and 3 (arrow between 2a and 3a in panel FIG. 7A) and plotted as a function of the local electric field during uni-A (FIGS. 7B, D, & F). In FIGS. 7C, E, & G, the ratio of the "CANCAN" and "asynchronized" exposures was plotted as a function of distance between the electrodes. Mean±S.E., n=5-8.

DETAILED DESCRIPTION

The present disclosure relates to methods and related aspects to target electrostimulation (ES) selectively to deep tissues and organs without inserting electrodes, which is accomplished, for example, by local superposition of bipolar stimuli of nanosecond duration. This paradigm increases the depth of penetration, selectivity, and precision of therapeutic and diagnostic treatments that utilize non-invasive ES. Exemplary applications of the ES method range from psychiatric disorders, Parkinson's disease, and pain control to targeted ablation of deep tumors, among many others.

Electrostimulation (ES) is widely used to manipulate biological function. Effects of ES are diverse and include nerve and muscle excitation, activation of immune and endocrine cells, cell differentiation, electroporation, etc. ES has well-established clinical applications including cardiac pacing, defibrillation, muscle training and rehabilitation, pain control, alleviation of Parkinson disease symptoms, diagnosis and treatment of neuromuscular and psychiatric disorders. Previously, the only way to target ES precisely to a specific area within the brain or body is by a direct stimulation with inserted or implanted electrodes. The tissue damage, pain, risks of bleeding, infection, and inflammation associated with electrode placement limit the use of this technique for examination of patients, disease diagnostics, and for treatments which do not justify the implantation surgery.

Figure 1:
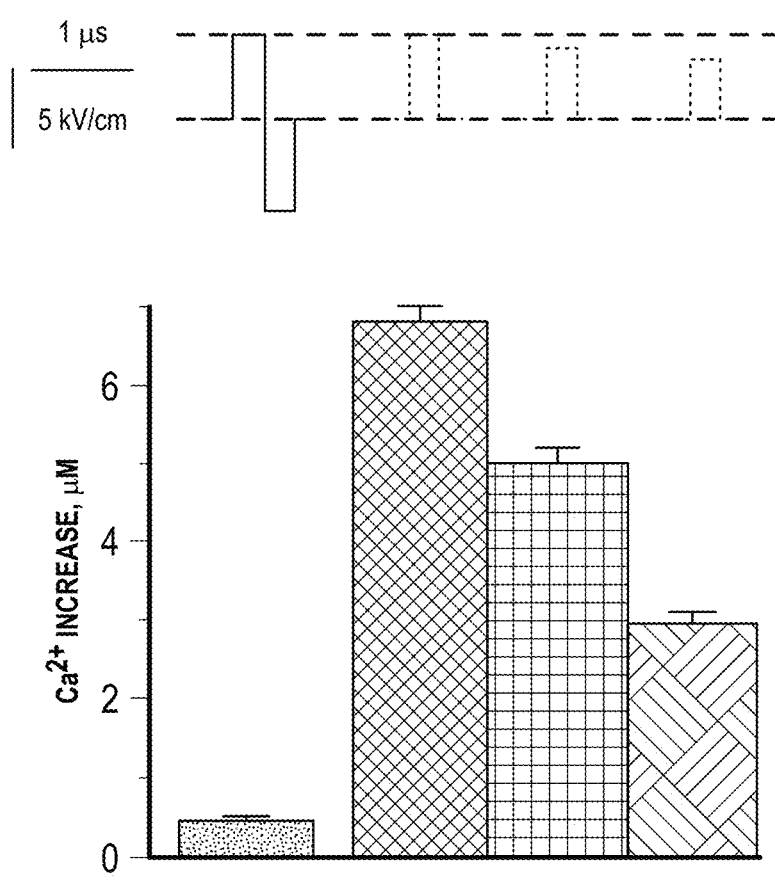
FIG. 1 shows $Ca^{2+}$ activation by bi and monopolar nsEP. Top: stimuli shapes and amplitudes according to one embodiment. Bottom: peak $Ca^{2+}$ response in CHO cells (mean+/−s.e., n=20-28).
Figure 2:
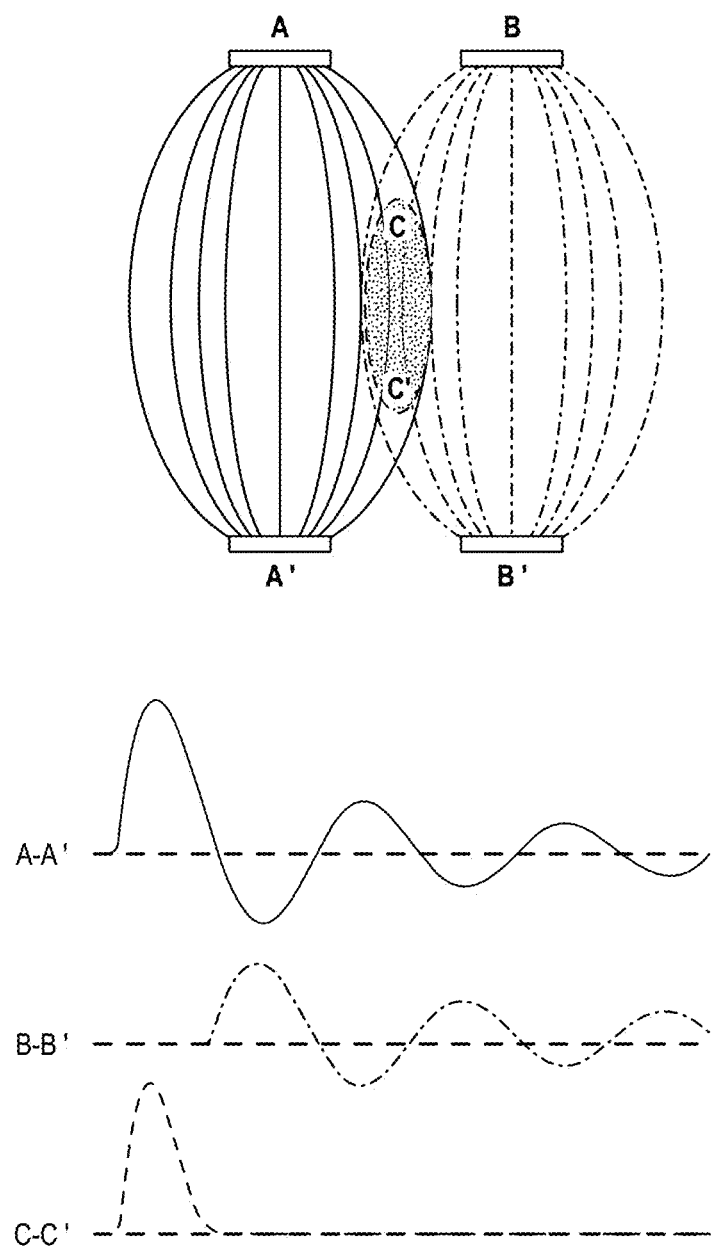
FIG. 2 shows the concept of remote ES by superposition of phased bipolar stimuli according to one embodiment. Upper: A-A' and B-B' are two pairs of ground-isolated stimulating electrodes. Dashed lines approximate the volumes to which the stimuli are delivered, with an overlap in the C-C' area. Lower: damped sine waves applied between A-A' and B-B' superpose into a monopolar pulse in the C-C' area.

The present disclosure provides a paradigm to enable selective, non-invasive, localized ES of deep targets. In certain embodiments, the disclosure relates to the use of the unique property of nanosecond electric pulses (nsEP) to cancel their stimulatory effect following the reversal of the stimulus polarity. In some embodiments, the second phase of a bipolar nsEP cancels the stimulatory effect of the 1st phase, hence the entire bipolar stimulus becomes weaker than a half of it (FIG. 1). In turn, superposing two bipolar stimuli into a monopolar stimulus cancels the cancellation (CANCAN) and restores the stimulus efficiency. An example in FIG. 2 shows how two damped sine waves produce a monopolar stimulus in the area C-C' away from the electrodes. This way, CANCAN enables ES selectively at a location remote from electrodes.

CANCAN effect is based on the phenomenon of bipolar cancellation. As also described in the Examples, the bipolar cancellation in diverse cell types (CHO, U937, cardiomyocytes) and using various endpoints ($Ca^{2+}$ mobilization, dye uptake, membrane conductivity, cell survival, phosphatidylserine externalization), and for nsEP of different duration and shape has been repeatedly demonstrated.

As described herein, the methods and related aspects are minimally disruptive (e.g., non-invasive). Competitive approaches typically require detachment of cells and spinning to transfer to different medium. These procedures are harmful or lethal to electroporated cells, thereby reducing the yield of transfected cells or rendering experiments non-feasible. The methods and related aspects disclosed herein also typically involve fewer procedural steps, lower cost, and fewer cells than pre-existing approaches. In addition, the methods and related aspects disclosed herein also involve the use of consistent and precisely defined electric fields, efficient media exchange and application/removal of drugs, and addition to aseptic conditions.

Electroporation (or electropermeabilization) describes the increase in membrane permeability that occurs upon exposure to high voltage electric pulses (EP) (4, 5). Electroporation has numerous biomedical applications including gene electrotransfer (8), electrochemotherapy (9), and tumor ablation by irreversible electroporation or $Ca^{2+}$ electroporation (10, 11). While conventional electroporation protocols utilize milli- and microsecond duration EP (ms- and µs-EP, respectively), more recent research has focused on EP of nanosecond duration (nsEP) (5, 12, 13). nsEP have distinct effects on cells compared to ms- and µs-EP, including the formation of nanometer-sized pores in the plasma membrane (14-16) as well as intracellular membranous structures (17-21), cytoskeletal reorganization and phospholipid scrambling (21-24), $Ca^{2+}$ mobilization (20, 25, 26), and the induction of cell death pathways (27-31).

A feature that is unique to nsEP, and clearly distinct from longer ms- and µs-EP has recently been reported (32-39). Cells exposed to a bipolar nsEP were electroporated less and had better cell survival compared to a unipolar nsEP of the same total duration (33). Likewise a bipolar nsEP that was twice the duration of a unipolar pulse caused less membrane permeabilization, despite delivering twice the energy (32). This attenuation of bioeffects by an electric field reversal has been termed "bipolar cancellation." This is because the application of a second opposite polarity pulse after the completion of the first pulse is able to undo, or "cancel," the effects of the first pulse. Bipolar cancellation has been shown in multiple cell types, and for different endpoints, including the transport of molecules and ions across the membrane (33, 34, 37-39), phosphatidylserine externalization (39), $Ca^{2+}$ mobilization (32, 36), and cell survival (32, 33). Bipolar cancellation continues for pulse separations as long as 10 µs (32) or even 50 µs (38). In contrast, two pulses of the same polarity caused two-fold greater permeabilization (38, 40). This cancellation effect has been observed for nsEP of different durations and shapes, including nanosecond electric field oscillations (NEFO) (34, 39) and asymmetrical bipolar nsEP with different amplitudes (39) or durations (37) for each phase. Notably, even when the second phase amplitude was reduced to 23% of the first phase, as is seen in NEFO, cancellation of effects was still observed. Hence, bipolar cancellation is a robust and reproducible phenomenon unique to nsEP that has not been observed for longer ms- and μs-EP (41-44).

The phenomenon of bipolar cancellation may explain the lack of biological effect from radiated electromagnetic pulses (45-47). Radiated electromagnetic pulses, including radiofrequency (RF) and ultra-wideband (UWB) emissions, are characterized by having extremely short pulse widths (in the nanosecond regime) and are inherently bipolar. Several studies have investigated the biological effects of radiated RF and UWB pulses, both in vitro (48-53) and in vivo (54-56), including those on cell growth and genotoxicity (48, 50, 52, 53), cardiac and neuronal excitability (49, 51), as well as cardiovascular, neurological, behavioral, locomotive, and developmental effects (45, 46, 54-56). The predominant finding from the various studies is that of no significant difference in effects from sham-exposed controls. Even the most powerful pulse exposures employed produced effects that were consistent with merely a thermal response. Interestingly, a "microwave hearing" effect is the only most widely accepted bioeffect of pulsed RF emissions (57). Therefore, the lack of biological effect and inefficiency of RF and UWB emissions is likely a consequence of bipolar cancellation.

Figure 3:
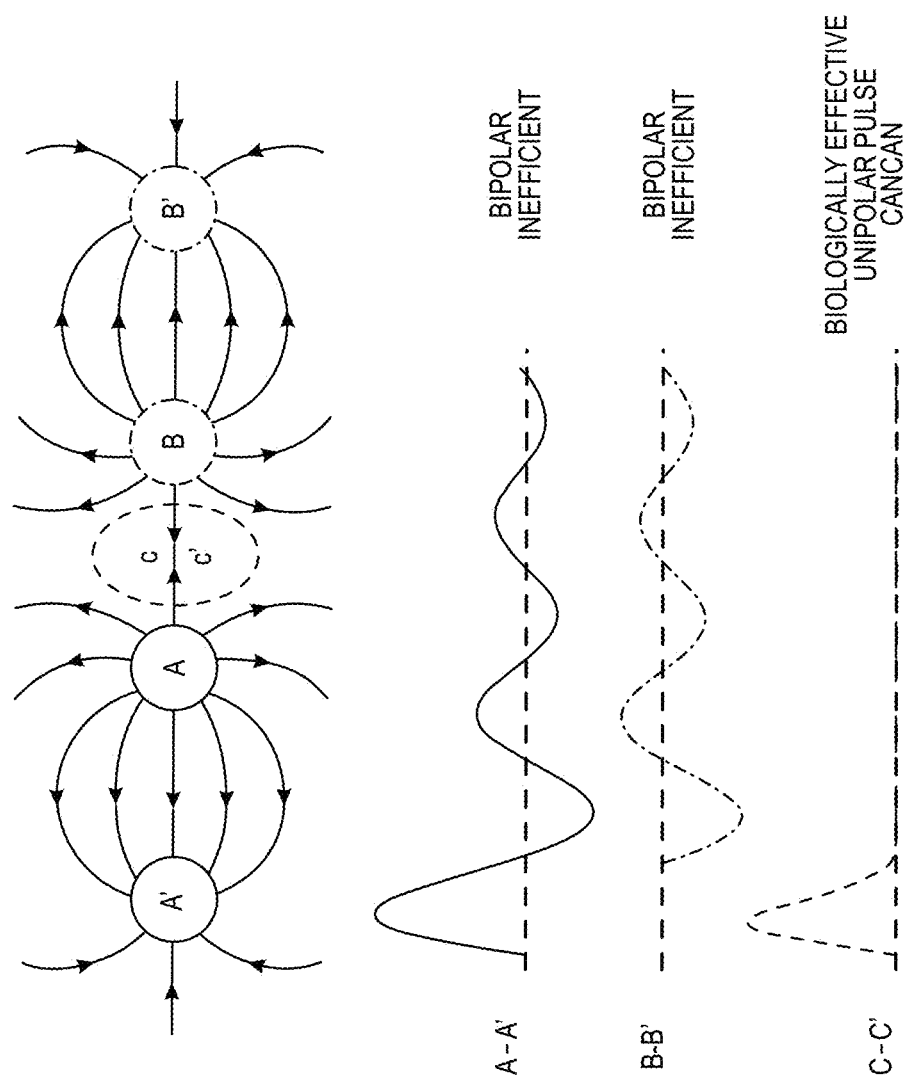
FIG. 3 shows a schematic illustrating the CANCAN concept according to one embodiment. Top: A-A' and B-B' are two independent pairs of nsEP-delivering electrodes. The dashed lines between A and B represent the area to which the E-field is delivered from each pair of electrodes, which overlap and nullify each other in the region C-C'. Bottom: Each pair of electrodes delivers a damped sine wave (DSW), which are per se biologically inefficient. When the DSW from B-B' is phase-shifted, the two DSW superpose into a biologically-effective unipolar pulse in the C-C' area. In this region, there is "cancellation of cancellation," or CANCAN.

In certain aspect, the present disclosure provides approaches to overcome the inherent inefficiency of bipolar nsEP for targeted, non-invasive electroporation or electrostimulation. This concept takes advantage of the fact that a bipolar nsEP on its own has a low biological efficiency. As illustrated in FIG. 3, a damped sine wave (DSW) applied between one pair of electrodes (A-A') is biologically ineffective. a second DSW that is phase-shifted (applied between electrodes B-B') is similarly ineffective. However, the superpositioning and synchronization of the two DSW creates a biologically effective unipolar pulse in a region distant from the two pairs of electrodes (C-C'). In other words, the effect of superpositioning the two biologically-ineffective DSW cancels the cancellation effect of the bipolar nsEP, creating a unipolar pulse. This concept is referred to as a "cancellation of cancellation", or CANCAN, effect.

Although various illustrative embodiments are described herein, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, this disclosure is provided primarily for exemplary purposes and should not be interpreted to limit the scope of the systems, apparatuses and methods described herein. This disclosure is intended to cover any and all adaptations or variations of various embodiments. Combinations of the embodiments described herein, and other embodiments not specifically described herein, will be apparent to those of skill in the art upon reviewing the above description.

EXAMPLES

Example 1

The cytosolic free $Ca^{2+}$ concentration ($[Ca^{2+}]_i$) was monitored by ratiometric fluorescence imaging with Fura-2 as reported previously[1,2]. In brief, cells loaded with the dye were placed in a glass-bottomed chamber mounted on an IX71 microscope (Olympus America, Center Valley, Pa.). The chamber was continually perfused with a solution containing (in mM): 140 NaCl, 5.4 KCl, 1.5 $MgCl_2$, 2 $CaCl_2$, 10 glucose, and 10 HEPES (pH 7.3, 290-300 mOsm/kg). For $Ca^{2+}$-free conditions, $CaCl_2$ was replaced with 2 mM Na-EGTA. In some experiments, $Ca^{2+}$ was depleted from the endoplasmic reticulum (ER) by preincubation with 10 μM of cyclopiazonic acid (CPA). Fura-2 was excited alternatively at 340 and 380 nm using a fast wavelength switcher Lambda DG4 (Sutter Instruments, Novato, Calif.). Emission was measured at 510 nm with an iXon Ultra 897 back-illuminated CCD camera (Andor Technology, Belfast, UK). $[Ca^{2+}]_i$ was calculated from Fura-2 emission ratio with Metafluor v.7.5 (Molecular Devices, Sunnyvale, Calif.).

Electric stimuli were delivered to selected cells on the coverslip with a pair of 0.1-mm diameter tungsten rods[3]. With an MPC-200 manipulator (Sutter), the rods were positioned precisely at 30 μm above the coverslip surface so that selected cells were in the middle of the 0.175-mm gap between their tips. The electric field was determined by 3D simulations with a finite-element Maxwell equation solver Amaze 3D (Field Precision, Albuquerque, N. Mex.). NsEP were triggered externally and synchronized with image acquisition by a TTL pulse protocol using Digidata 1440A board and Clampex v. 10.2 software (Molecular Devices). The pulse traces were captured with a TDS 3052 oscilloscope (Tektronix, Beaverton, Oreg.). Hereinafter, the reported amplitude of bipolar pulses is the amplitude of the first phase. Each cell was exposed only once.

Example 2

In this example, the feasibility of the CANCAN concept was further tested. Using two independent pairs of nsEP-delivering electrodes, the permeabilization of CHO-K1 cells embedded in an agarose gel was measured. It was found that the synchronization and superpositioning of two nsEP caused an enhancement in permeabilization in a region distant from each pair of stimulating electrodes, that was equal to that of a unipolar pulse. Hence, for the first time a proof-of-concept of the creation of a biologically effective unipolar pulse remotely by superpositioning two independent nsEP, demonstrating successful CANCAN was shown. Optimization of this technology has many implications for non-invasive, deep-tissue electroporation or electrostimulation.

Materials and Methods

Cell Line and Media

Chinese hamster ovary (CHO-K1) cells were purchased from the American Type Culture Collection (ATCC, Manassas, Va.). Cells were cultured in F-12K medium (Mediatech Cellgro, Herndon, Va.) supplemented with 10% fetal bovine serum (Atlanta Biologicals, Flowery Branch, Ga.), 100 IU/mL penicillin, and 0.1 μg/mL streptomycin (Gibco Laboratories, Gaithersburg, Md.).

Three-Dimensional Cell Culture

On the day of experiments, cells were embedded in an agarose gel three-dimensional (3D) culture, similar to previously described methods (55). Briefly, the bottom of a 60 mm dish was coated with 7 mL of 2% low-gelling-temperature agarose (Sigma-Aldrich, St. Louis, Mo.) in F-12K growth medium. Cells were harvested and resuspended in 0.75% agarose in the growth medium at a concentration of $5\times10^6$ cells/mL; 4 mL of this suspension was deposited dropwise over the 2% agarose base layer in a 60 mm dish. The dishes were incubated at 4° C. for 5 minutes to hasten agarose jellification and prevent cell sedimentation, and then transferred to the incubator for at least 30 minutes before nsEP exposure. YO-PRO-1 iodide (YP; 1 µM in PBS; Thermo Fisher Scientific, Waltham, Mass.) was added to each dish 5 minutes prior to nsEP exposures and incubated at 37° C. to allow the dye to equilibrate throughout the agarose gel.

Figure 4A:
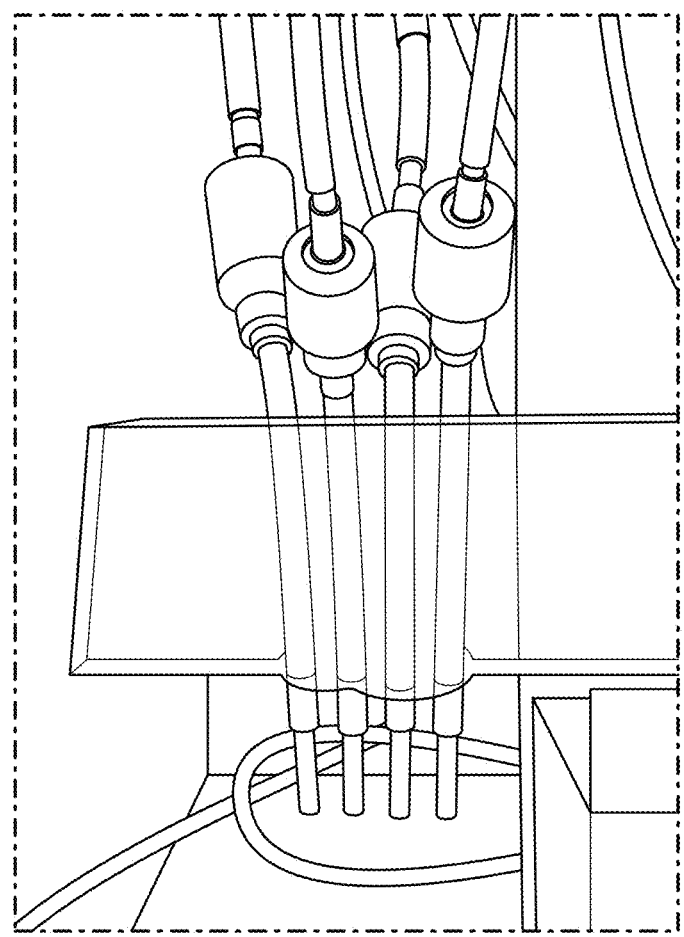
FIGS. 4A-C show an exemplary modeling of electrodes used for CANCAN experiments according to one embodiment.

Electrodes and nsEP Exposures nsEP delivery to cells embedded in agarose 3D cultures was accomplished using two pairs of stainless steel needle electrodes arranged in a linear array (FIG. 4A; 1.66 mm in diameter with a 2 mm interelectrode spacing). Each pair of electrodes was connected to an independent nsEP-delivering channel, with electrodes 1 and 2 connected to Channel 1 and electrodes 3 and 4 connected to Channel 2 (FIG. 4C). Electrodes 2 and 3, positioned in the center of the linear array, were active (a), and electrodes 1 and 4, on the periphery, were ground (g). The linear array was mounted on a micromanipulator to enable accurate and steady insertion of the electrodes into an agarose gel containing cells.

nsEP were produced using a combination of three separate MOSFET-based pulse generators, as recently described (59), that were each capable of producing a unipolar or bipolar nsEP, and two separate high-voltage DC power supplies. Each generator consisted of two stacks of fundamental modules, each containing a charging capacitor and a MOSFET switch, which produced either a positive or negative pulse to the desired voltage. The three generators were combined to produce a multiphasic pulse generator, which was subsequently connected to the electrodes via two independent nsEP-delivering channels (see above). A digital delay generator (model 577-8C, Berkeley Nucleonics Corporation, San Rafael, Calif.) was used to control the pulse duration (600 ns for each phase) and delay between each phase. The exact shape and amplitude of the nsEP were monitored using a Hantek DSO5202P oscilloscope (Qingdao, Shandong Province, China). The amplitude of each phase was expressed as a percentage of the first (with the first being equal to 100%), and indicated in the corresponding figure legend. Hereinafter, the reported pulse amplitude and electric field intensity are those measured at the peak of the first phase of the nsEP delivered from Channel 1.

In each experiment, cells were exposed to 100, 600-ns EP (10 Hz) as one of the following exposure conditions: unipolar from Channel 1; bipolar from Channel 1 (biphasic or triphasic); unipolar from Channel 2; bipolar from Channel 2 (biphasic); "CANCAN" exposure (Channel 1 and Channel 2 nsEP synchronized and phase-shifted); asynchronized (Channel 1 and Channel 2 nsEP delivered 10 ms apart); sham (no nsEP delivered). For accurate comparison, all nsEP and sham exposures were performed in a random order in the same cell sample, with up to 8 exposures per 60 mm dish. All nsEP exposures were conducted at room temperature (22±2° C.).

nsEP Dosimetry and CANCAN Modeling

A 3D model, matching the experimental conditions, was implemented using the commercial finite element method solver COMSOL Multiphysics®, Release 5.0 (COMSOL Inc., Stockholm, Sweden).

Figure 4B:
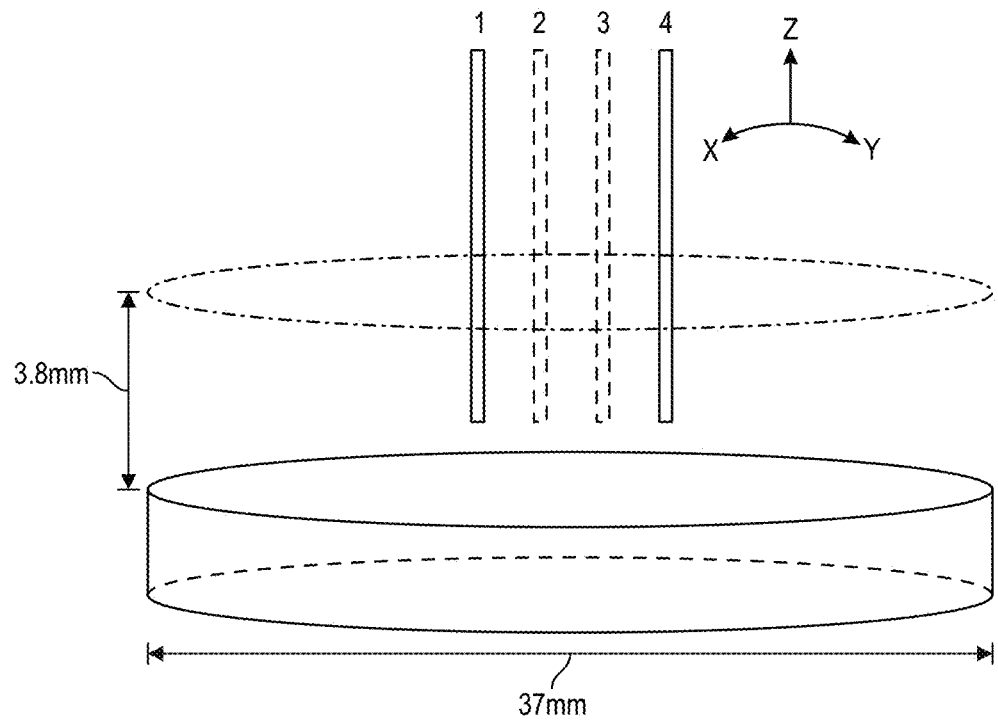
Figure 4C:
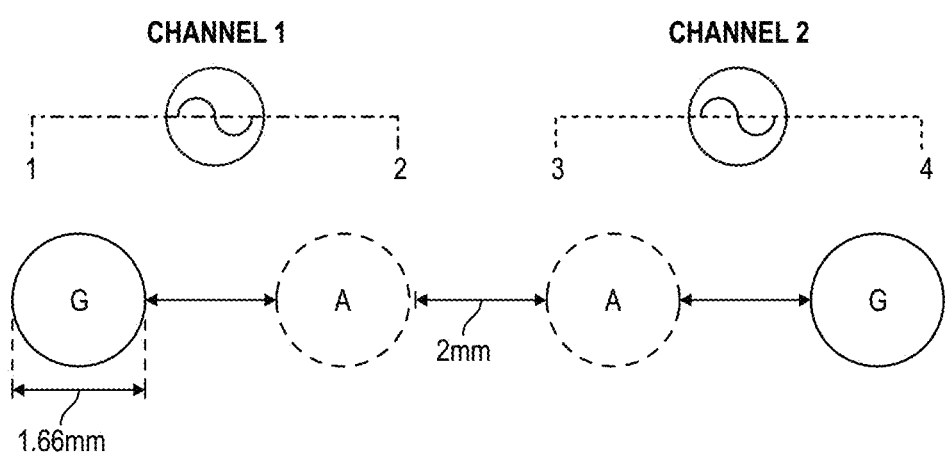

Two pairs of stainless steel needle electrodes (1.66 mm diameter, 3 cm height) were arranged in a linear array (2 mm interelectrode distance), as shown in FIGS. 4B & C. The electrodes were immerged in a solution with conductivity 1.4 S/m and relative permittivity 76 and positioned 1 mm above the bottom of the petri dish. The latter was modeled as a dielectric cylinder (35 mm diameter, 2 mm thickness) with relative permittivity 3.8. The system described was surrounded by a sphere (35 mm diameter) of air.

The tetrahedral mesh chosen to discretize the domain of simulation resulted in a mesh element minimum size of 0.10 mm, a maximum size of 2.45 mm, and a total number of elements 401,038 in a volume of simulation of 22449.3 $mm^3$. Quadratic elements were used throughout the solution domain, giving $0.54 \times 10^6$ degrees of freedom.

The Electric Currents interface was used to solve Maxwell's equations in steady-state conditions, for which:

$$\nabla \cdot (-\sigma \nabla V) = 0 \quad (1)$$

where V is the electric potential used to compute the electric field, $E = -\nabla V$, and the current, $J = \sigma E$, where $\sigma$ is the conductivity of the media. Under electrostatic conditions, the dispersive properties of the media were disregarded.

During the experiments, properly synchronized and delayed multiphasic rectangular pulses were delivered by two Channels (FIG. 5A), each connected to two electrodes. The amplitude of phase A was taken as reference (100%), and that of each subsequent phase was set as a percentage of A. Two pulse exposures were modeled, 100/70/40% and 100/50/25%.

In the simulations each phase combination was modeled separately. When phase A was delivered by Channel 1, electrodes 1 and 4 were set as ground, 1 V was applied to electrode 2, and electrode 3 was disconnected from the circuit. When the phases B and D were delivered by Channels 1 and 2, respectively, electrodes 1 and 4 were set as ground, while either −0.7 (70%) or −0.5 (50%) V were applied at both electrodes 2 and 3. Finally, when phases C and E were delivered by Channels 1 and 2, respectively, electrodes 1 and 4 were set as ground, and either 0.4 (40%) or 0.25 (25%) V were applied at both electrodes 2 and 3.

Figure 5A:
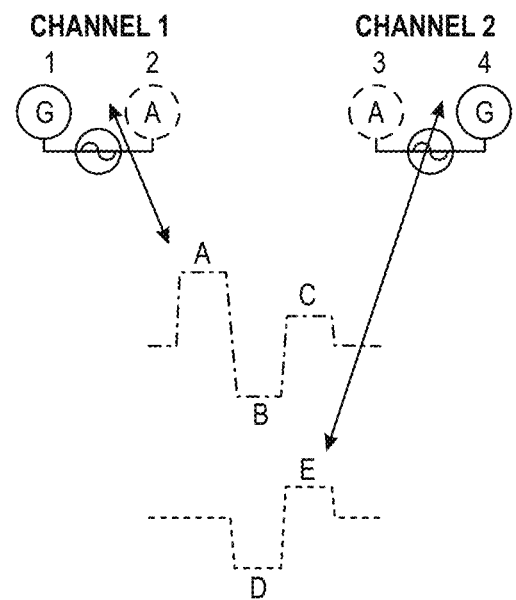
FIGS. 5A-D show exemplary electric field dosimetry and nullification efficiency according to one embodiment.

Superposition of Two Multiphasic Pulses Produces Distinct Regions of Unipolar and Bipolar Exposure Numerical simulations of the |E| distribution produced by the array of electrodes of FIG. 5A were computed to provide the dosimetry for the experimental study and to validate the CANCAN concept. This approach takes advantage of the spatial superposition of two multiphasic pulses: the E-field produced by the two Channels sum up for components of same direction, while subtract when opposite, producing a unipolar exposure in a region distant from the electrodes, and bipolar elsewhere. The CANCAN concept ensures a reduction of the biological effect in the region of bipolar exposure, i.e. in proximity to the electrodes, and enhancement between them where only a unipolar pulse is delivered.

Figure 5B:
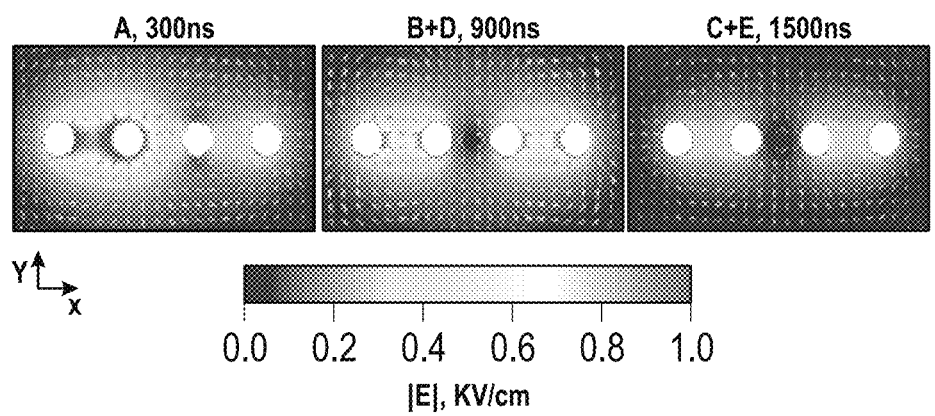

FIG. 5B shows the |E| distribution for the different phase combinations in the xy plane perpendicular to the electrodes at 3.8 mm from the petri dish, i.e. in correspondence to the layer of cells. When only Channel 1 was active (FIG. 5B, panel A) |E| was more intense between electrodes 1 and 2, and decayed toward electrode 4. Electrode 3 was not grounded, therefore it produced only a distortion of the E-field. When both Channels delivered an electric voltage of the same polarity (FIG. 5B, panels B+D and C+E), the subtraction of the E components of opposite direction produced a reduction of |E| in the area between electrodes 3 and 4.

Figure 5C:
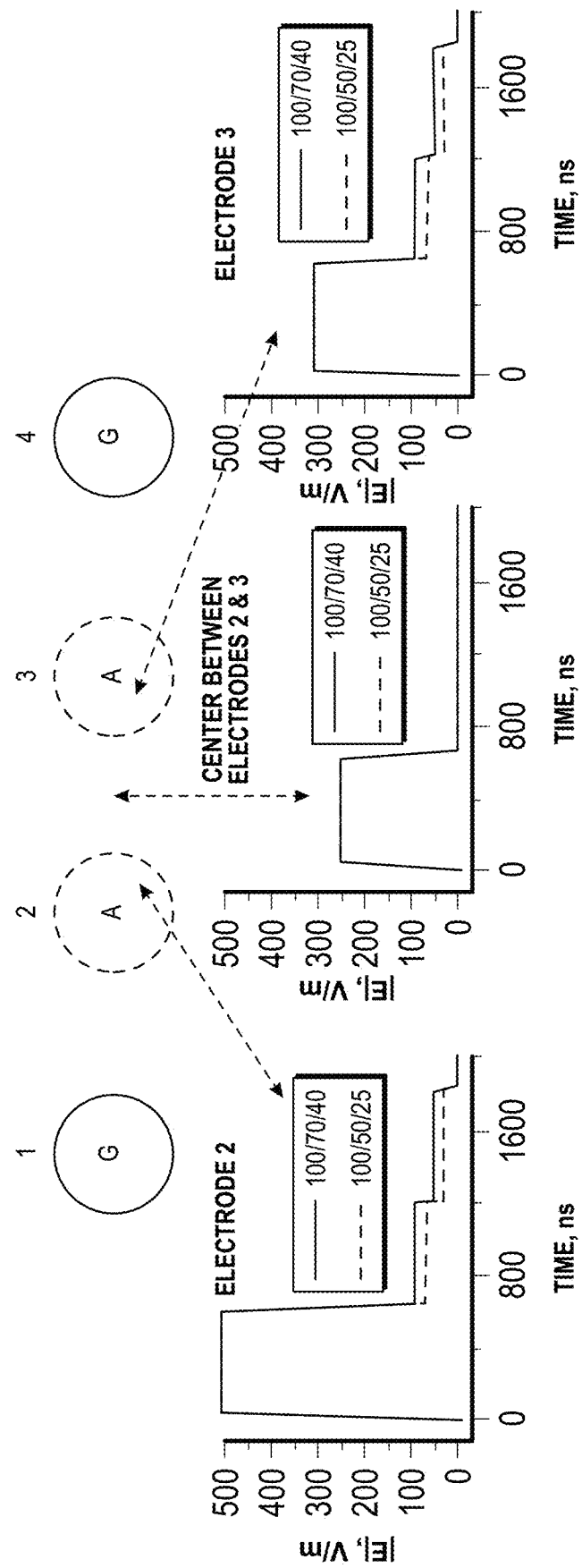

From FIG. 5B the E-field was extracted as a function of time for three points, two near either electrode 2 or 3 and one at the center between them. FIG. 5C shows that |E| was maximum during phase A (0-600 ns). During the delivery of the subsequent phases (600-1800 ns), |E| was completely abolished (0 kV/cm) at the center between electrodes 2 and 3, resulting in a unipolar pulse. Whereas, near the edges of the electrodes, this reduction was ~20%, indicating bipolar exposure.

This reduction in a region of 3.6×3.6 mm was quantified between electrodes 2 and 3 computing:

$$R\% = \frac{|E(A)| - |E(B+F)|}{|E(A)|} \times 100 \quad (2)$$

Figure 5D:
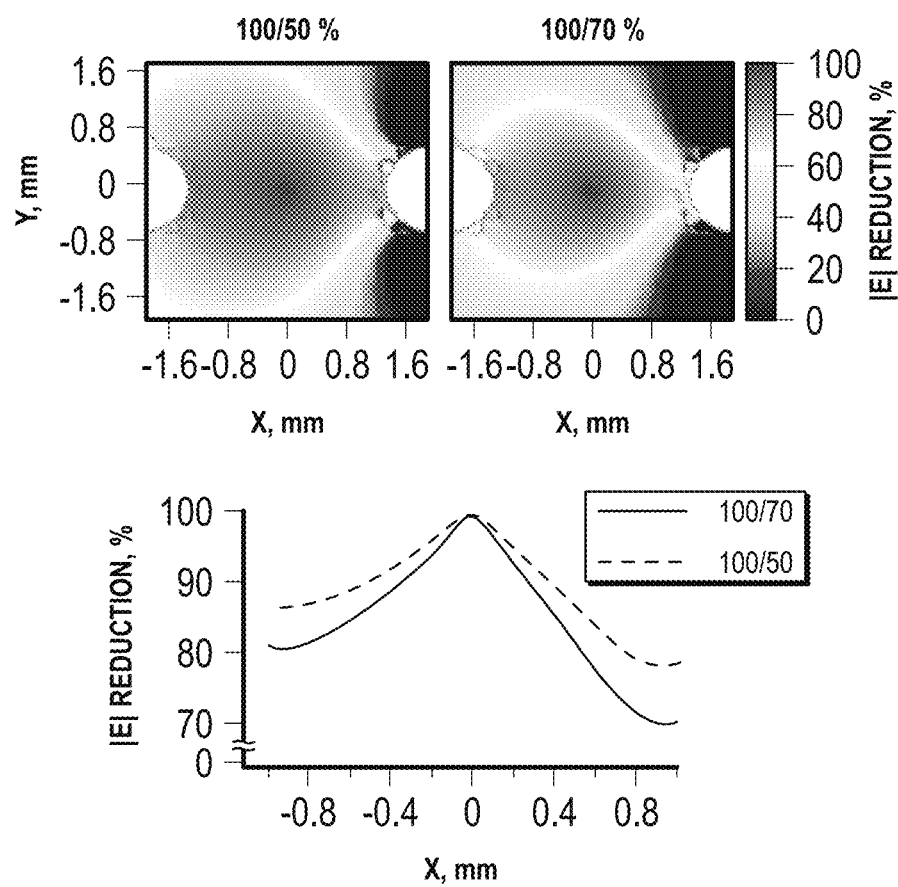

FIG. 5D shows R % for 100/50% and 100/70%. For both cases, the reduction was maximum in the center between the electrodes, with a steeper decay for 100/70% exposure. Plotting R % as a function of x highlights this difference (FIG. 5D, upper right panel), suggesting the 100/70% condition may offer a more efficient and targeted CANCAN effect.

Cell Imaging and Data Processing

After nsEP exposures, dishes were kept covered for 15 minutes, and then washed 5 times with PBS to remove all YP. Images of electropermeabilized cells were acquired using an Olympus SZX16 fluorescence stereo microscope (Olympus America, Hamden, Conn.) equipped with a Hamamatsu C9100 EM-CCD camera (Hamamatsu, Shizuoka Prefecture, Japan) and a 0.8×, 0.12 NA objective. YP emission was detected using an X-Cite Series 120Q fluorescence light source (Excelitas Technologies Corporation, Waltham, Mass.) and a GFP filter (ex. 460-490 nm/em. 510-).

Images were quantified using MetaMorph 7.8.13 software (Molecular Devices, Foster City, Calif.). The YP fluorescence was measured within 16 regions of interest (ROI) drawn along the x-plane between electrodes 2 and 3 and plotted as a function of distance from the center between the electrodes (mm; see FIGS. 4A-C). For each image, the fluorescence intensity within each ROI was corrected for the background fluorescence. Data are presented as mean±SE for n independent experiments.

Results

Synchronization of a Bipolar and Unipolar nsEP Causes an Enhancement in Electroporation In the CANCAN hypothesis, the superpositioning and synchronization of two properly shaped bipolar nsEP, which are per se inefficient, restores a biologically effective unipolar pulse remotely (see FIG. 3). This is because, at a certain location distant from the electrodes, the E-field produced during each subsequent phase which coincide in time nullify one another, so that what remains is only the first phase as a unipolar pulse. This nullification occurs when the E-field components from the two independent nsEP are opposite in direction, producing an |E| intensity of 0 kV/cm in that region (see FIGS. 5A-D and Materials and Methods).

Figure 6A:
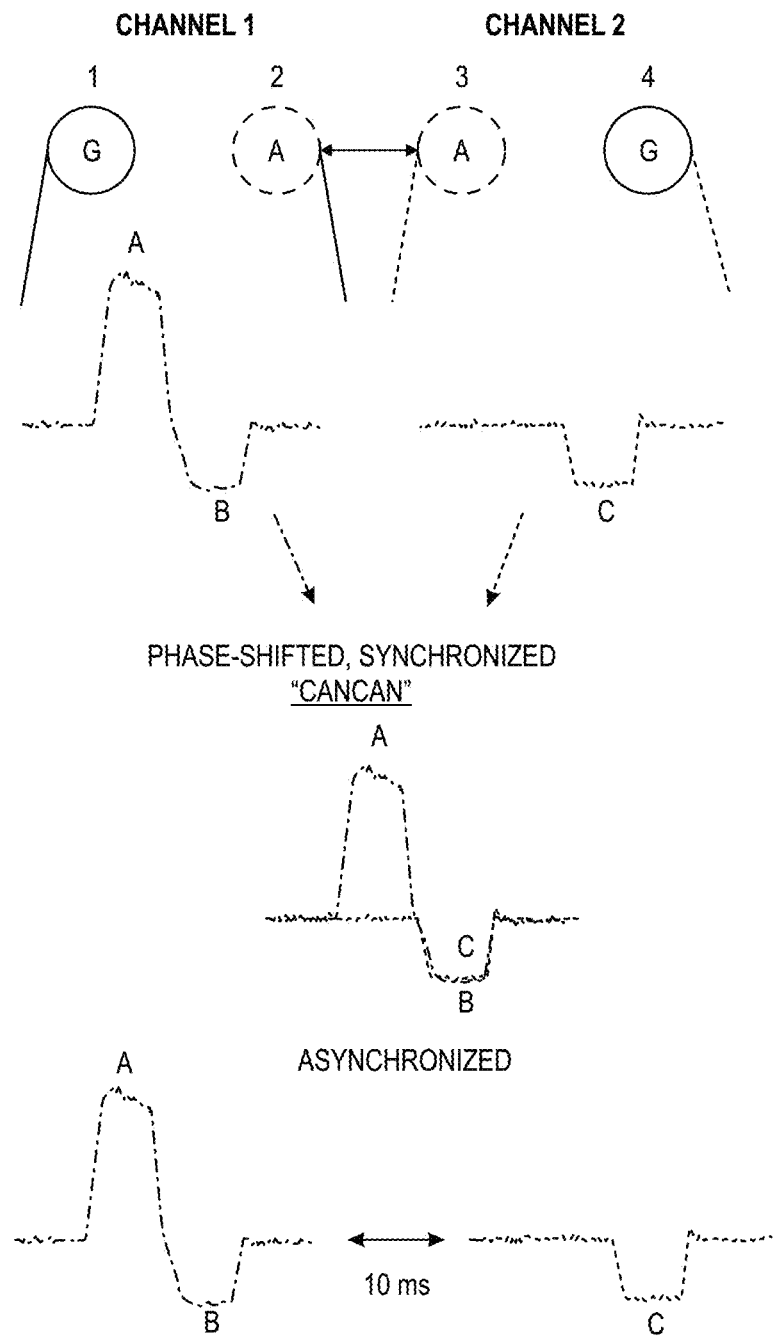
FIGS. 6A-D show superpositioning of a bipolar and unipolar nsEP causes CANCAN remotely according to one embodiment.
Figure 6B:
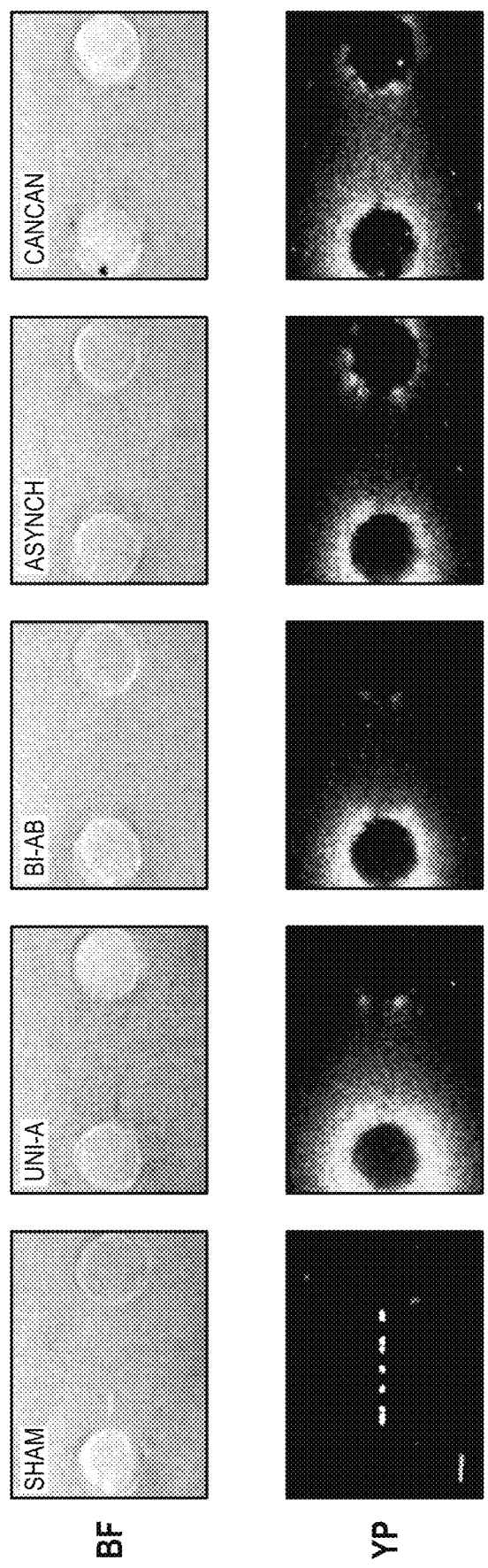
Figure 6C:
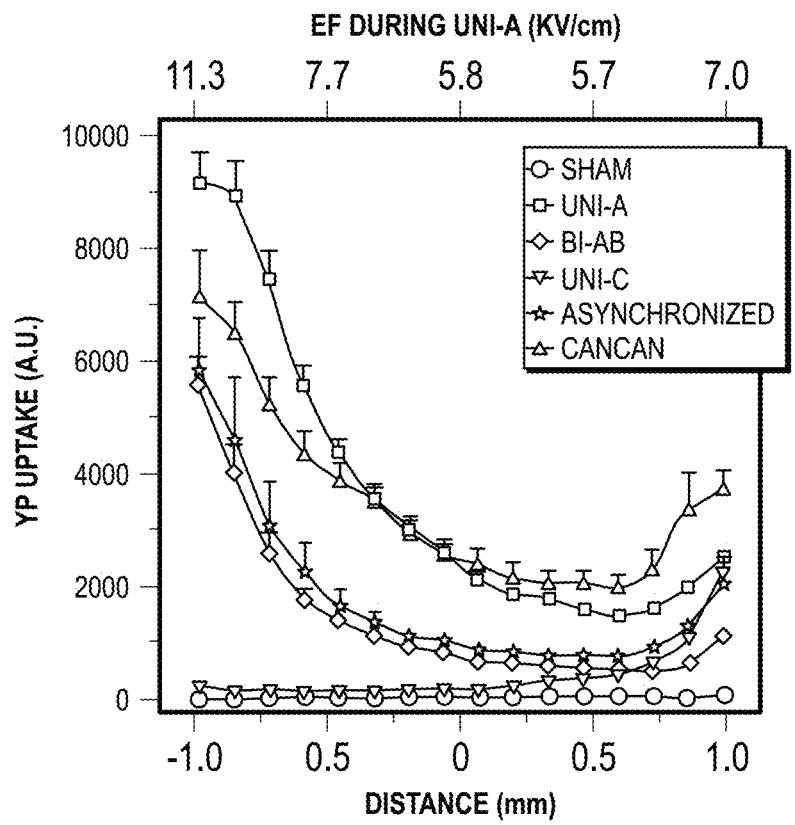

As a first approach to test CANCAN experimentally, we evaluated the potential for E-field nullification with only 2 opposite polarity phases (FIGS. 6A-D). Successful CANCAN depends, at least in part, on the extent of bipolar cancellation. Therefore, the amplitude of the second phase was made 50% of the first based on previous results which showed bipolar cancellation was maximal with a 50% second phase amplitude for trapezoidal nsEP (39). E-field modeling predicted maximal E-field nullification, and in turn a maximal CANCAN effect, to be in the center between electrodes 2 and 3 (see Materials and Methods). Therefore, we focused on this region (i.e. along the X-plane between electrodes 2 and 3) to assess the biological effect (FIG. 6B).

Figure 6D:
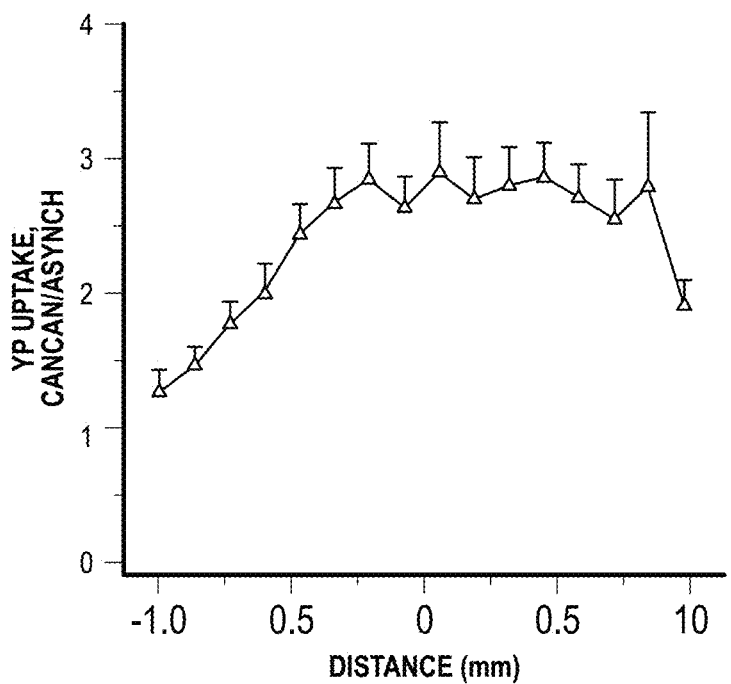

We measured electropermeabilization in CHO-K1 cells embedded in an agarose gel by the uptake of the YO-PRO-1 (YP) dye. Using two independent pairs of nsEP-delivering electrodes, cells were exposed to either unipolar or bipolar nsEP from one or both pairs of electrodes (100, 600 ns, 10 Hz). Channel 1 electrodes (1 and 2) delivered a unipolar (uni-A) or bipolar nsEP (bi-AB); Channel 2 electrodes (3 and 4) delivered a unipolar pulse (uni-C) that was phase-shifted so that it coincided with the second phase of bi-AB when delivered synchronously ("CANCAN" exposure; FIG. 6A). We found that bi-AB caused a ~2-3-fold reduction in permeabilization compared to uni-A along the entire length between the electrodes (FIGS. 6B & C), indicating successful bipolar cancellation in a 3D culture model. Permeabilization by uni-C was greatest near electrode 3 (the active electrode in Channel 2), and decreased with increasing distance from electrode 3. When bi-AB and uni-C were delivered asynchronously (i.e. with a 10-ms delay between them), the electropermeabilization effect was not different from bi-AB along most of the length between the electrodes. Closer to electrode 3, the effect became more similar to that of uni-C as the impact from Channel 2 electric field was felt. In contrast, the synchronized delivery of bi-AB and uni-C caused an enhancement of permeabilization across the entire length between the electrodes that was maximally ~3-fold greater than asynchronous delivery in the center between the electrodes (FIG. 6D). Notably, the extent of permeabilization at the center was equal to that of the uni-A exposure, consistent with the E-field modeling results. Hence, these findings demonstrate the remote creation of a biologically effective unipolar pulse by the synchronized delivery of a bipolar and unipolar nsEP, and thus reveal successful CANCAN.

Synchronization of Multiphasic nsEP Further Enhances Electroporation Remotely

Figure 7A:
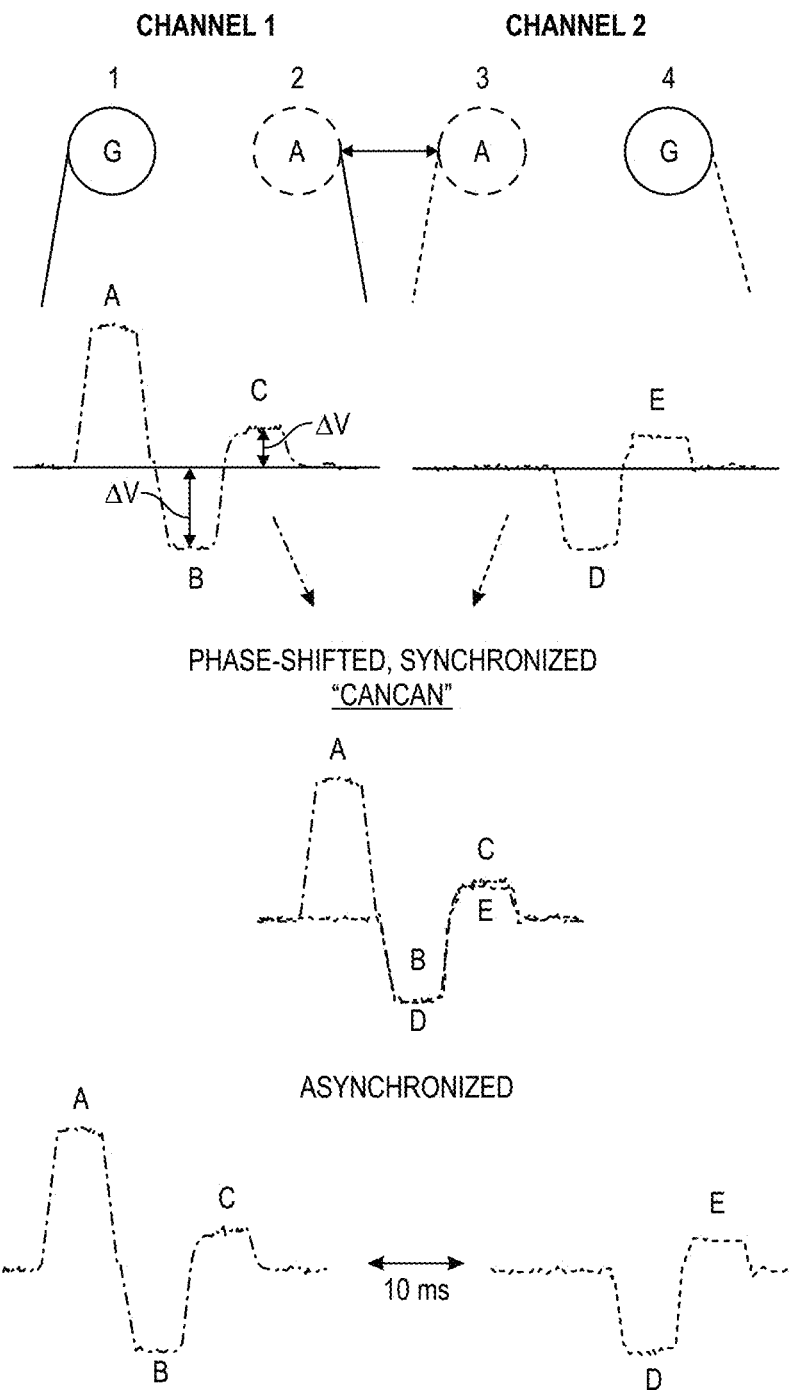
FIGS. 7A-G show exemplary synchronization of multiphasic nsEP improves the CANCAN effect according to one embodiment.

In the previous experiments, we showed that it is possible to produce a unipolar pulse remotely by nullification of the E-field delivered from two independent pairs of electrodes. Therefore, in the next set of experiments, we evaluated the efficiency of E-field nullification, and in turn CANCAN, with the addition of a third opposite polarity phase (FIGS. 7A-G). Channel 1 electrodes delivered a triphasic bipolar nsEP (bi-ABC), and Channel 2 delivered a biphasic nsEP (bi-DE) so that phases D and E coincided with phases B and C from bi-ABC, respectively (FIG. 7A). The amplitude of the second phase was kept at 50% of the first, and the third phase was likewise reduced by half to be 25% of phase A. Notably, the amplitudes of phases C and E were not entirely matched in these experiments, due to the limitations of the pulser, whereby the amplitudes were ~20% and 30% of phase A, respectively. Because each phase was within 5% of the targeted 25% phase amplitude, we nonetheless conducted the experiment with the slightly mismatched amplitudes.

Figure 7B:
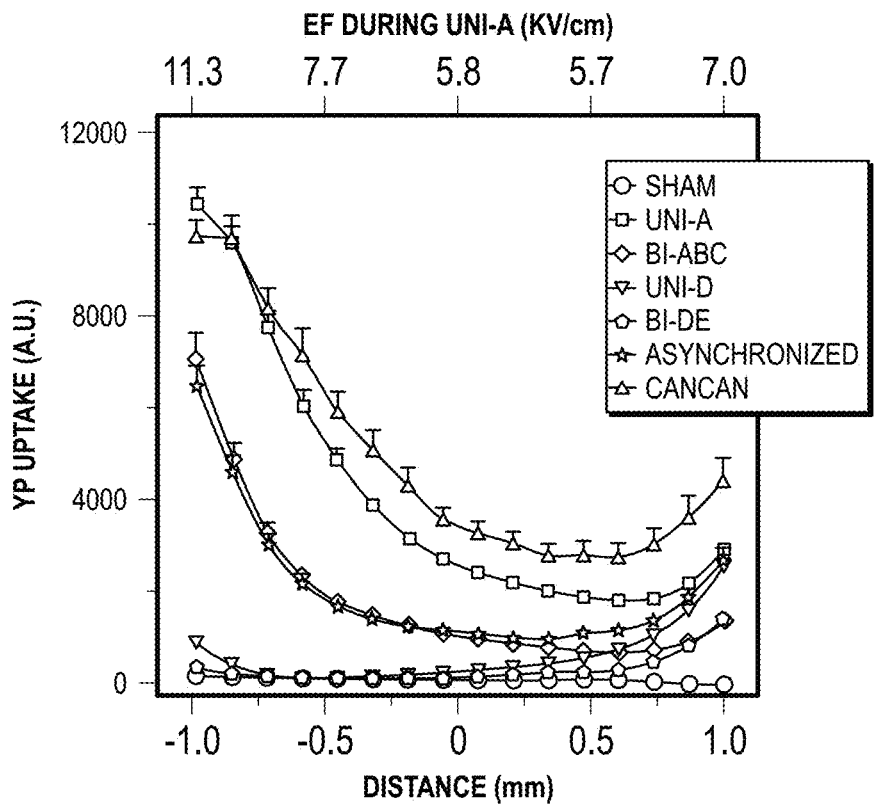
Figure 7C:
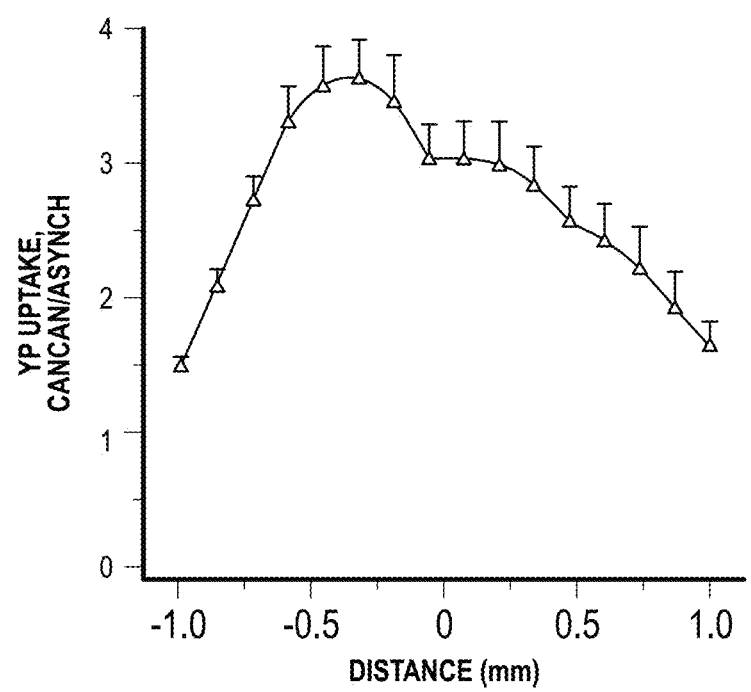

We found that the bi-ABC from Channel 1 caused cancellation of permeabilization, with a ~2-3-fold reduction in YP uptake compared to uni-A, revealing bipolar cancellation occurs with triphasic nsEP (FIG. 7B). Likewise, bi-DE delivered from Channel 2 caused a ~2-fold reduction in permeabilization compared to uni-D. Hence, each bipolar nsEP on its own had a relatively low biological efficiency. Delivering the two bipolar nsEP asynchronously did not enhance the permeabilization effect. Near Channel 1 electrodes, the extent of permeabilization was similar to that of bi-ABC; closer to electrode 3, the impact of the combined E-field from both channels resulted in a permeabilization effect that was essentially additive of that from bi-ABC and bi-DC. This additive effect was not seen near Channel 1 primarily because the effect of bi-DC was very small near electrode 2 (near zero), offering a negligible contribution to the degree of permeabilization. When the two bipolar nsEP were delivered synchronously, the permeabilization effect was profoundly enhanced compared to asynchronous delivery (~3-4-fold greater; FIGS. 7B & C), and was more similar (and in fact, greater) to that of uni-A in the center. The enhanced permeabilization by synchronized delivery that was greater than uni-A exposures in the center may be due to the slight mismatch in the amplitudes of phases C and E. This could potentially result in incomplete nullification of E during the third phase, producing a residual E-field that was not reduced and contributed to the overall biological effect. Nonetheless, we show a CANCAN effect with the superpositioning of two inefficient bipolar nsEP to create a biologically efficient nsEP remotely.

Figure 7D:
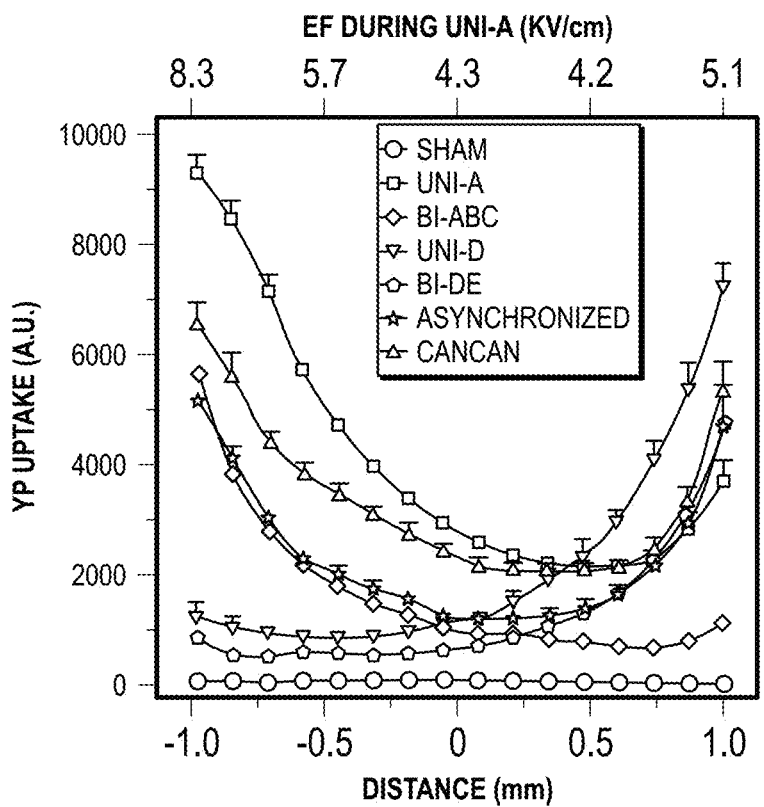
Figure 7E:
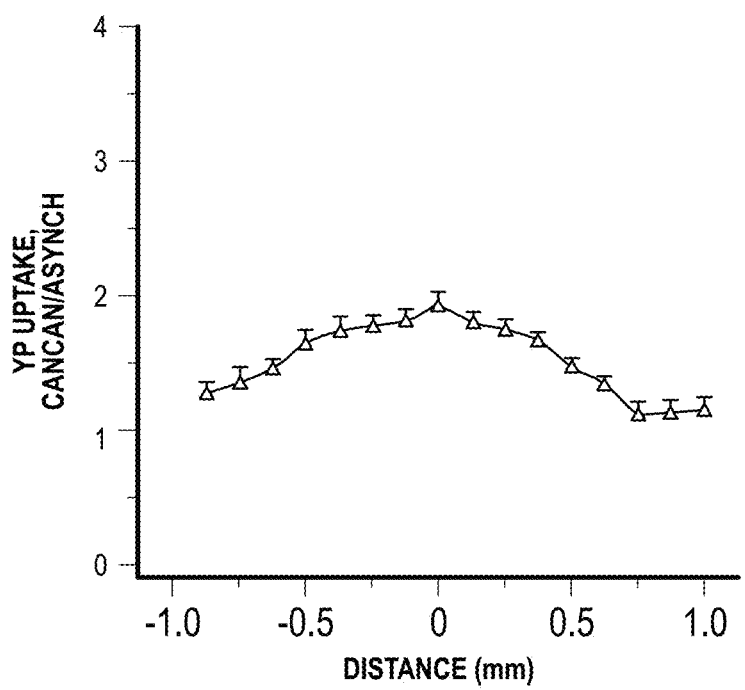

Increasing the Amplitude of the Subsequent Opposite Polarity Phases Improves CANCAN One of the main goals for successful CANCAN is to have a lower effect compared to a unipolar pulse near the nsEP-delivering electrodes, while creating an effect equal to that of unipolar remotely. While in the previous experiments, we successfully created a biologically equivalent unipolar nsEP in the center between the electrodes, the biological effect was still similar to or greater than that of a unipolar pulse near the electrodes. Therefore, we sought to improve our CANCAN effect by modifying the nsEP parameters. The E-field modeling results predicted that a second phase amplitude of 70% may offer less E-field nullification near the electrodes than a 50% second phase amplitude (see FIGS. 5A-D). This, in turn, may result in better bipolar cancellation near the electrodes when the two nsEP are delivered synchronously. Therefore, as a first approach, we increased the amplitude of only the second phase to be 70% of phase A, while the amplitude of the third phase remained at 25%. As in the previous experiments, Channel 1 delivered a bi-ABC triphasic nsEP, and Channel 2 a bi-DE biphasic nsEP. Consistent with the previous results, bi-ABC and bi-DE caused ~2-3-fold less permeabilization than uni-A and uni-D, respectively, across the entire length between electrodes 2 and 3 (FIG. 7D). The two delivered asynchronously created a permeabilization effect that was similar to each bipolar nsEP individually. That is, near electrode 2, the extent of permeabilization was similar to that of bi-ABC, while closer to electrode 3, the effect was similar to bi-DE. Synchronizing the delivery of the two bipolar nsEP enhanced the permeabilization effect in the center between the electrodes, that was ~2-fold greater than asynchronous delivery (FIG. 7E) and similar to that of uni-A. Given a bipolar cancellation efficiency of ~2-fold, an enhancement in permeabilization of ~2-fold in the center is the maximum we can theoretically expect if we assume complete E-field nullification. Notably, closer to the electrodes, the extent of permeabilization was less than that of the unipolar nsEP delivered from each channel (i.e. uni-A from Channel 1 and uni-D from Channel 2), and was not different from asynchronous delivery near electrode 3. Combined, these results suggest that with a second phase amplitude of 70%, there is less E-field nullification near the electrodes, causing the bipolar cancellation effect to predominate. In contrast, in the center between the electrodes, the effect is maximally different from asynchronous delivery and similar to that of uni-A exposures, indicating maximal E-field nullification and CANCAN.

Figure 7F:
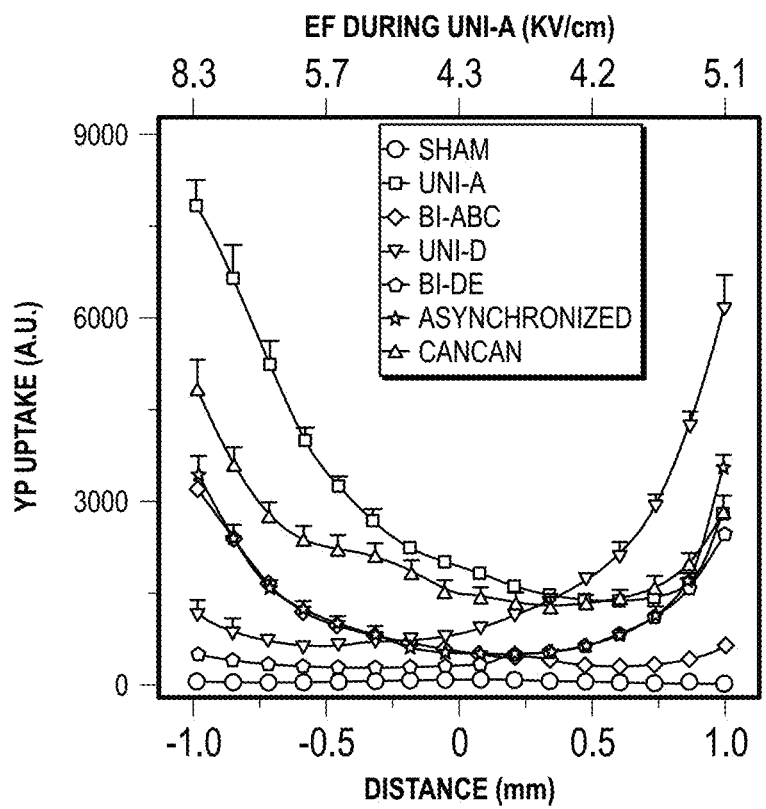
Figure 7G:
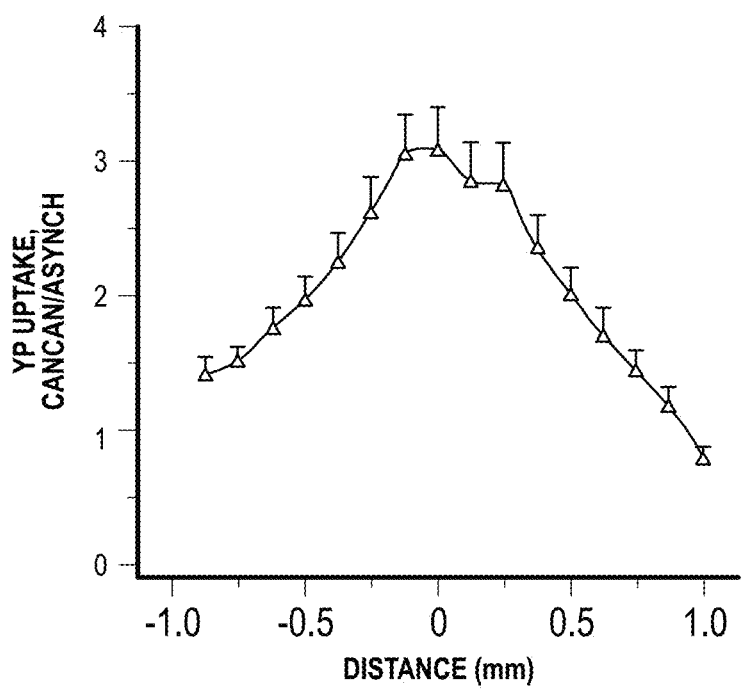

As a next step, we wanted to enhance the bipolar cancellation efficiency in an effort to further improve the remote CANCAN effect. To do this, we increased the amplitude of the third phase to 40% of phase A (so that it was reduced by a similar extent as the second phase), which may in turn offer better bipolar cancellation. The amplitude of the second phase was kept at 70%, as in the previous set of experiments. We found that increasing the amplitude of the third phase of bi-ABC to 40% increased the efficiency of bipolar cancellation, so that permeabilization was reduced by ~3-4-fold compared to uni-A in the center between the electrodes (FIG. 7F). The biphasic bi-DE caused a reduction in permeabilization of ~2-3-fold compared to uni-D, indicating the cancellation efficiency was not further enhanced by increasing the amplitude of phase E. When the two nsEP were delivered asynchronously, the permeabilization effect was not different from either bipolar nsEP delivered individually. However, synchronized delivery of bi-ABC and bi-DE caused an enhancement in permeabilization in the center between the electrodes similar to that of uni-A and ~3-fold greater than asynchronous delivery (FIG. 7G). The difference in effect between synchronous and asynchronous nsEP delivery matched closely with the degree of bipolar cancellation, suggesting complete E-field nullification in the center region. As in the previous results, closer to the electrodes the permeabilization effect was less than that of either unipolar exposure, and became more similar to asynchronous delivery. In other words, closer to the electrodes, there is less E-field nullification, and instead, bipolar cancellation predominates. Interestingly, the curve produced when plotting the ratio of synchronized to asynchronized exposures (FIG. 7G) was reminiscent in shape to the percent reduction curve shown in FIG. 5D, further validating the E-field modeling results. Hence, increasing the amplitude of the third phase increased the efficiency of bipolar cancellation, which in turn, improved and enhanced the efficiency of CANCAN in the center between the electrodes.

Discussion

In this study, we show for the first time the remote electroporation by the superpositioning of two biologically ineffective bipolar nsEP into a biologically effective unipolar pulse. This effect, termed cancellation of cancellation, or CANCAN, occurs when the E-field produced during the coincident phases of each bipolar nsEP are opposite in direction and nullify each other, leaving only a unipolar exposure in a region distant from the electrodes, while remaining bipolar elsewhere. Consequently, CANCAN relies on the inherent inefficiency of bipolar nsEP for targeted electroporation. Synchronizing the delivery of two independent nsEP caused up to 3-fold greater electroporation remotely than asynchronous nsEP delivery (i.e. delivered 10 ms apart). This isolated enhancement of electroporation by CANCAN was reproducibly observed in different sets of experiments with varying nsEP parameters. Hence, we present a proof-of-concept for the CANCAN concept to cause targeted and remote electroporation.

The efficiency of CANCAN is expected to be directly proportional to the extent of bipolar cancellation achieved. Therefore, in each set of experiments, we modified the nsEP parameters, including the number and amplitude of phases, to test the efficiency of bipolar cancellation, and in turn, CANCAN. We observed successful CANCAN both when applying biphasic, as well as triphasic nsEP. The most efficient CANCAN effect occurred when using triphasic nsEP with phase amplitudes that were 100/70/40% of the first phase (FIGS. 7F & G). This was unexpected if we consider our previous results which showed a second phase amplitude of 50% provided the best cancellation efficiency (39). Based on the results from our previous study, we can speculate that a 40% second phase amplitude may cancel bioeffects to a similar extent as a 50% amplitude. Thus, it is possible that the addition of the third phase at 40% amplitude caused sufficient cancellation on its own, which when combined with the effect from the second phase, enhanced the overall bipolar cancellation efficiency. Notably, our experimental results corroborated the predictions made in the E-field modeling (FIGS. 5A-D). Quantifying the percent reduction of E for different phase amplitudes indicated there was less reduction of E near the electrodes when the second phase was 70% of the first, suggesting a more targeted CANCAN effect. In fact, our experimental results demonstrate this, whereby the synchronized delivery of the two nsEP produced an effect that was maximally ~3-fold greater than asynchronous delivery remotely, consistent with the degree of bipolar cancellation, while being not different near the electrodes where bipolar cancellation was predominant. Hence, in the region where maximal E-field nullification was expected, the enhancement in electroporation by CAN-CAN was the maximum theoretically possible based on the extent of bipolar cancellation. Thus, using a combination of E-field modeling and experimental approaches, we show the most efficient targeted electroporation by CANCAN occurs with nsEP amplitudes of 100/70/40% of the first phase.

The formation of a unipolar pulse remotely by CANCAN presents the potential to access deep targets non-invasively. While our results present the proof-of-concept for remote electroporation by CANCAN, the CANCAN effect may likewise extend to electrostimulation. As such, the potential biomedical applications of CANCAN are numerous and include: ablation of deep-seated tumors and/or blood metastases by electroporation, deep brain stimulation for the treatment of various neurological or psychological disorders (e.g. Parkinson's disease, epilepsy, or depression), pain control, and cardiac defibrillation. Current therapeutic approaches employing either electroporation or electrostimulation are invasive and require the insertion or implantation of contact electrodes (60, 61). Consequently, they carry the usual risks associated with surgery, including inflammation, infection or bleeding. Non-invasive techniques for electrostimulation, including transcranial magnetic stimulation (TMS), transcutaneous electrical nerve stimulation (TENS), and transcranial direct current stimulation (tDCS), are limited by either a lack of precision for the target and/or poor penetration depth (60, 62). Hence the need to develop a technique for non-invasive electroporation or electrostimulation is warranted. A recent study evaluated the potential to use two temporally interfering electric fields for non-invasive deep brain stimulation (63). They showed that two high frequency electric fields delivered concurrently caused neuronal stimulation at a location within the hippocampal layer of the brain. Their approach is based on a long-standing phenomenon related to acoustic waves (64). In short, when two subthreshold stimuli with a fixed amplitude are delivered simultaneously, they sum up to create a lower frequency oscillating electric field envelope with a suprathreshold amplitude. In other words, their approach relies on the summation of two subthreshold stimuli to create a stimulus whose amplitude is suprathreshold remotely. In contrast, electrostimulation or electroporation by CANCAN uniquely relies instead on a change in the shape of the pulse from bipolar into unipolar, rather than on a change in the pulse amplitude or duration. Thus, the CANCAN concept is novel and presents the potential to selectively electroporate or electrostimulate deep targets, while sparing superficial tissue. Our study provides the basis for the development of advanced technologies for CAN-CAN. One potential development of CANCAN would utilize pulsed RF transmitters which may focus to a target deep in the body.

In summary, we present here a proof-of-concept for the remote electroporation by a CANCAN effect. We show that the synchronized delivery of two nsEP caused an enhancement in electroporation remotely that was maximally ~3-fold greater than asynchronous delivery, and similar to that of a unipolar exposure. The remote enhancement in electroporation by CANCAN was reproducible in different sets of experiments, using varying nsEP parameters. The development of the CANCAN concept into advanced technologies presents the potential to non-invasively electroporate or electrostimulate targets deep in the body.

REFERENCES

1. Semenov, I., Xiao, S. & Pakhomov, A. G. Primary pathways of intracellular Ca(2+) mobilization by nanosecond pulsed electric field. *Biochim Biophys Acta* 1828, 981-9 (2013).
2. Semenov, I., Xiao, S., Pakhomova, O. N. & Pakhomov, A. G. Recruitment of the intracellular Ca by ultrashort electric stimuli: The impact of pulse duration. *Cell Calcium* 15, 00083-3 (2013).
3. Pakhomov, A. G. et al. Long-lasting plasma membrane permeabilization in mammalian cells by nanosecond pulsed electric field (nsPEF). *Bioelectromagnetics* 28, 655-663 (2007).
4. Teissie J, Eynard N, Gabriel B, & Rols M P (1999) Electropermeabilization of cell membranes. Advanced drug delivery reviews 35(1):3-19.
5. Pakhomov A G, Miklavcic D, & Markov M S eds (2010) Advanced Electroporation Techniques in Biology and Medicine (CRC Press, Boca Raton), p 528.
6. Tsong T Y (1991) Electroporation of cell membranes. Biophysical journal 60(2):297-306.
7. Tarek M (2005) Membrane electroporation: a molecular dynamics simulation. Biophysical journal 88(6):4045-4053.
8. Neumann E (1992) Membrane electroporation and direct gene transfer. Bioelectrochemistry and Bioenergetics 28(1):247-267.
9. Miklavcic D, Mali B, Kos B, Heller R, & Sersa G (2014) Electrochemotherapy: from the drawing board into medical practice. Biomedical engineering online 13(1):29.
10. Frandsen S K, et al. (2012) Direct therapeutic applications of calcium electroporation to effectively induce tumor necrosis. Cancer Res 72(6):1336-1341.
11. Davalos R V, Mir I L, & Rubinsky B (2005) Tissue ablation with irreversible electroporation. Annals of biomedical engineering 33(2):223-231.
12. Schoenbach K H, et al. (2007) Bioelectric effects of intense nanosecond pulses. Ieee Transactions on Dielectrics and Electrical Insulation 14(5):1088-1109.
13. Batista Napotnik T, Reberšek M, Vernier P T, Mali B, & Miklavčič D (2016) Effects of high voltage nanosecond electric pulses on eukaryotic cells (in vitro): A systematic review. Bioelectrochemistry 110:1-12.
14. Pakhomov A G, et al. (2009) Lipid nanopores can form a stable, ion channel-like conduction pathway in cell membrane. Biochemical and biophysical research communications 385(2):181-186.
15. Ho M C, Casciola M, Levine Z A, & Vernier P T (2013) Molecular dynamics simulations of ion conductance in field-stabilized nanoscale lipid electropores. The journal of physical chemistry. B 117(39):11633-11640.

16. Pakhomov A G, et al. (2015) Multiple nanosecond electric pulses increase the number but not the size of long-lived nanopores in the cell membrane. Biochimica et biophysica acta 1848(4):958-966.
17. Batista Napotnik T, Wu Y H, Gundersen M A, Miklavcic D, & Vernier P T (2012) Nanosecond electric pulses cause mitochondrial membrane permeabilization in Jurkat cells. Bioelectromagnetics 33(3):257-264.
18. Beebe S J, Chen Y J, Sain N M, Schoenbach K H, & Xiao S (2012) Transient features in nanosecond pulsed electric fields differentially modulate mitochondria and viability. PLoS One 7(12):e51349.
19. Semenov I, Xiao S, & Pakhomov A G (2013) Primary pathways of intracellular Ca(2+) mobilization by nanosecond pulsed electric field. Biochimica et biophysica acta 1828(3):981-989.
20. Semenov I, Xiao S, Pakhomova O N, & Pakhomov A G (2013) Recruitment of the intracellular Ca2+ by ultrashort electric stimuli: the impact of pulse duration. Cell Calcium 54(3):145-150.
21. Thompson G L, et al. (2016) Permeabilization of the nuclear envelope following nanosecond pulsed electric field exposure. Biochemical and biophysical research communications 470(1):35-40.
22. Vernier P T, Sun Y, Marcu L, Craft C M, & Gundersen M A (2004) Nanoelectropulse-induced phosphatidylserine translocation. Biophysical journal 86(6):4040-4048.
23. Pakhomov A G, et al. (2014) Disassembly of actin structures by nanosecond pulsed electric field is a downstream effect of cell swelling. Bioelectrochemistry 100: 88-95.
24. Tolstykh G P, Beier H T, Roth C C, Thompson G L, & Ibey B L (2014) 600 ns pulse electric field-induced phosphatidylinositol4,5-bisphosphate depletion. Bioelectrochemistry 100:80-87.
25. Vernier P T, Sun Y, Chen M T, Gundersen M A, & Craviso G L (2008) Nanosecond electric pulse-induced calcium entry into chromaffin cells. Bioelectrochemistry 73(1):1-4.
26. Craviso G L, Choe S, Chatterjee I, & Vernier P T (2012) Modulation of intracellular Ca2+ levels in chromaffin cells by nanoelectropulses. Bioelectrochemistry 87:244-252.
27. Beebe S J, Fox P M, Rec L J, Willis E L, & Schoenbach K H (2003) Nanosecond, high-intensity pulsed electric fields induce apoptosis in human cells. FASEB J 17(11): 1493-1495.
28. Ren W, Sain N M, & Beebe S J (2012) Nanosecond pulsed electric fields (nsPEFs) activate intrinsic caspase-dependent and caspase-independent cell death in Jurkat cells. Biochemical and biophysical research communications 421 (4):808-812.
29. Pakhomova O N, Gregory B W, Semenov I, & Pakhomov A G (2013) Two modes of cell death caused by exposure to nanosecond pulsed electric field. PLoS One 8(7):e70278.
30. Morotomi-Yano K, Akiyama H, & Yano K (2014) Different involvement of extracellular calcium in two modes of cell death induced by nanosecond pulsed electric fields. Arch Biochem Biophys 555-556:47-54.
31. Ullery J C, Tarango M, Roth C C, & Ibey B L (2015) Activation of autophagy in response to nanosecond pulsed electric field exposure. Biochemical and biophysical research communications 458(2):411-417.
32. Pakhomov A G, et al. (2014) Cancellation of cellular responses to nanoelectroporation by reversing the stimulus polarity. Cellular and molecular life sciences: CMLS 71 (22):4431-4441.
33. Ibey B L, et al. (2014) Bipolar nanosecond electric pulses are less efficient at electropermeabilization and killing cells than monopolar pulses. Biochemical and biophysical research communications 443(2):568-573.
34. Gianulis E C, et al. (2015) Electroporation of mammalian cells by nanosecond electric field oscillations and its inhibition by the electric field reversal. Scientific reports 5:13818.
35. Schoenbach K H, et al. (2015) Ion transport into cells exposed to monopolar and bipolar nanosecond pulses. Bioelectrochemistry 103:44-51.
36. Merla C, Pakhomov A G, Semenov I, & Vernier P T (2017) Frequency spectrum of induced transmembrane potential and permeabilization efficacy of bipolar electric pulses. Biochimica et biophysica acta 1859(7):1282-1290.
37. Valdez C M, et al. (2017) Asymmetrical bipolar nanosecond electric pulse widths modify bipolar cancellation. Scientific reports 7(1):16372.
38. Gianulis E C, Casciola M, Xiao S, Pakhomova O N, & Pakhomov A G (2018) Electropermeabilization by uni- or bipolar nanosecond electric pulses: The impact of extracellular conductivity. Bioelectrochemistry 119:10-19.
39. Pakhomov A G, et al. (2018) The second phase of bipolar, nanosecond-range electric pulses determines the electroporation efficiency. Bioelectrochemistry 122:123-133.
40. Semenov I, Casciola M, Ibey B L, Xiao S, & Pakhomov A G (2018) Electropermeabilization of cells by closely spaced paired nanosecond-range pulses. Bioelectrochemistry 121:135-141.
41. Tekle E, Astumian R D, & Chock P B (1991) Electroporation by using bipolar oscillating electric field: an improved method for DNA transfection of NIH 3T3 cells. Proceedings of the National Academy of Sciences of the United States of America 88(10):4230-4234.
42. Kotnik T, Miklavcic D, & Mir L M (2001) Cell membrane electropermeabilization by symmetrical bipolar rectangular pulses. Part II. Reduced electrolytic contamination. Bioelectrochemistry 54(1):91-95.
43. Kotnik T, Mir L M, Flisar K, Puc M, & Miklavcic D (2001) Cell membrane electropermeabilization by symmetrical bipolar rectangular pulses. Part I. Increased efficiency of permeabilization. Bioelectrochemistry 54(1): 83-90.
44. Kotnik T, Pucihar G, Rebersek M, Miklavcic D, & Mir L M (2003) Role of pulse shape in cell membrane electropermeabilization. Biochimica et biophysica acta 1614(2):193-200.
45. Seaman R L (2007) Effects of exposure of animals to ultra-wideband pulses. Health physics 92(6):629-634.
46. Schunck T, Bieth F, Pinguet S, & Delmote P (2016) Penetration and propagation into biological matter and biological effects of high-power ultra-wideband pulses: a review. Electromagnetic biology and medicine 35(1):84-101.
47. Pakhomov A G, Akyel Y, Pakhomova O N, Stuck B E, & Murphy M R (1998) Current state and implications of research on biological effects of millimeter waves: a review of the literature. Bioelectromagnetics 19(7):393-413.
48. Pakhomova O N, Belt M L, Mathur S P, Lee J C, & Akyel Y (1998) Ultra-wide band electromagnetic radiation does not affect UV-induced recombination and mutagenesis in yeast. Bioelectromagnetics 19(2):128-130.
49. Pakhomov A G, et al. (2000) Comparative effects of extremely high power microwave pulses and a brief CW irradiation on pacemaker function in isolated frog heart slices. Bioelectromagnetics 21(4):245-254.
50. Pakhomov A G, Gajsek P, Allen L, Stuck B E, & Murphy M R (2002) Comparison of dose dependences for bioeffects of continuous-wave and high-peak power microwave emissions using gel-suspended cell cultures. Bioelectromagnetics 23(2):158-167.
51. Pakhomov A G, Doyle J, Stuck B E, & Murphy M R (2003) Effects of high power microwave pulses on synaptic transmission and long term potentiation in hippocampus. Bioelectromagnetics 24(3):174-181.
52. Chemeris N K, et al. (2006) Lack of direct DNA damage in human blood leukocytes and lymphocytes after in vitro exposure to high power microwave pulses. Bioelectromagnetics 27(3):197-203.
53. Ibey B L, et al. (2016) Cellular effects of acute exposure to high peak power microwave systems: Morphology and toxicology. Bioelectromagnetics.
54. Jauchem J R, et al. (1998) Ultra-wideband electromagnetic pulses: lack of effects on heart rate and blood pressure during two-minute exposures of rats. Bioelectromagnetics 19(5):330-333.
55. Lu S T, et al. (2000) Effects of high peak power microwaves on the retina of the rhesus monkey. Bioelectromagnetics 21(6):439-454.
56. Cobb B L, et al. (2000) Neural and behavioral teratological evaluation of rats exposed to ultra-wideband electromagnetic fields. Bioelectromagnetics 21(7):524-537.
57. Lin J C & Wang Z (2007) Hearing of microwave pulses by humans and animals: effects, mechanism, and thresholds. Health physics 92(6):621-628.
58. Muratori C, Pakhomov A G, Xiao S, & Pakhomova O N (2016) Electrosensitization assists cell ablation by nanosecond pulsed electric field in 3D cultures. Scientific reports 6:23225.
59. H. A. Ryan S H, E. Yang, C. Zhou and S. Xiao (2018) High-Voltage, Multiphasic, Nanosecond Pulses to Modulate Cellular Responses. IEEE Transactions on Biomedical Circuits and Systems (99):1-13.
60. Nizard J, Lefaucheur J P, Helbert M, de Chauvigny E, & Nguyen J P (2012) Non-invasive stimulation therapies for the treatment of refractory pain. Discovery medicine 14(74):21-31.
61. Miklavcic D & Davalos R V (2015) Electrochemotherapy (ECT) and irreversible electroporation (IRE)—advanced techniques for treating deep-seated tumors based on electroporation. Biomedical engineering online 14 Suppl 3:11.
62. Roth Y, Amir A, Levkovitz Y, & Zangen A (2007) Three-dimensional distribution of the electric field induced in the brain by transcranial magnetic stimulation using figure-8 and deep H-coils. Journal of clinical neurophysiology: official publication of the American Electroencephalographic Society 24(1):31-38.
63. Grossman N, et al. (2017) Noninvasive Deep Brain Stimulation via Temporally Interfering Electric Fields. Cell 169(6):1029-1041 e1016.
64. Dmochowski J & Bikson M (2017) Noninvasive Neuromodulation Goes Deep. Cell 169(6):977-978.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of generating a biologically effective unipolar electric pulse, the method comprising superposing a first biologically ineffective bipolar electric pulse generated from a first stimuli and a second biologically ineffective bipolar electric pulse generated from a second stimuli to create the biologically effective unipolar electric pulse at a location remote from the first and second stimuli.

2. The method of claim 1, wherein the biologically effective unipolar electric pulse has an enhanced stimulus efficiency as compared to the first or second biologically ineffective bipolar electric pulse generated in the absence of the superposing step,
    wherein the first or second biologically ineffective bipolar electric pulse generated in the absence of the superposing step induces a cancellation effect caused by a second phase of the first or second biologically ineffective bipolar electric pulse cancelling or reducing a stimulatory effect of a first phase of the first or second biologically ineffective bipolar electric pulse, and
    wherein the enhanced stimulus efficiency of the biologically effective unipolar electric pulse is caused by cancelling or reducing the cancellation effect.

3. The method of claim 1, wherein the first stimuli comprises a first pair of electrodes and the second stimuli comprises a second pair of electrodes, the first and second pair of electrodes each connected to an independent electric pulse-delivering channel.

4. The method of claim 3, wherein the first and second pair of electrodes is each aligned in a linear array.

5. The method of claim 1, wherein the unipolar electric pulse is non-invasively delivered to a subject.

6. The method of claim 5, wherein the unipolar electric pulse is non-invasively delivered to a localized cell, tissue or organ in the subject.

7. The method of claim 6, wherein the tissue is a deep tissue.

8. The method of claim 1, wherein the unipolar electric pulse is delivered to a sample.

9. The method of claim 1, wherein the method is used for one or more of the following: selectively targeting deep tissue of a subject, diagnosing and treating neuromuscular and psychiatric disorders, treating Parkinson's disease, ablation of deep tissue, pain control, nerve and muscle excitation, activation of immune and endocrine cells, electroporation, cardiac pacing, defibrillation, muscle training and rehabilitation, or deep brain stimulation.

10. The method of claim 2, wherein the enhanced stimulus efficiency of the biologically effective unipolar electric pulse is directionally proportional to the extent of cancellation or reduction of the cancellation effect.

11. The method of claim 1, wherein the first and/or second biologically ineffective bipolar electric pulses are biphasic or triphasic.

12. The method of claim 1, wherein the first and/or second biologically ineffective bipolar electric pulses have at least a first and second phase and the amplitude of the second phase is between 25% and 100% of the first.

13. The method of claim 1, wherein either one or both of the first biologically ineffective bipolar electric pulse and the second biologically ineffective bipolar electric pulse comprises one or more phases.

14. The method of claim 1, wherein at least one of the first biologically ineffective bipolar electric pulse and the second biologically ineffective bipolar electric pulse has a duration of up to 1800 nanoseconds.

15. The method of claim 1, wherein at least one of the first or the second biologically ineffective bipolar electric pulse has multiple phases and at least one phase of the multiple phases has different duration or amplitude than another phase of the multiple phases.

16. The method of claim 1, wherein either one or both of the first biologically ineffective bipolar electric pulse and the second biologically ineffective bipolar electric pulse comprises damped electric pulses.

17. A method of generating a monopolar electric pulse, the method comprising superposing at least a first electric pulse generated from at least a first electric pulse-delivering channel and at least a second electric pulse generated from at least a second electric pulse-delivering channel to create the monopolar electric pulse at a location remote from the first and second channels, wherein a number of phases of the first electric pulse differs from a number of phases of the second electric pulses by one phase.

18. The method of claim 17, wherein the first and second electric pulses are each bipolar.

19. The method of claim 17, wherein the first electric pulse is bipolar and wherein the second electric pulse is unipolar.

20. The method of claim 17, wherein at least one of the first and second electric pulses is uniphasic or multiphasic, and the at least first electric pulse and the at least a second electric pulse are damped.

21. The method of claim 17, wherein the first and second channels each comprise an active electrode.

22. The method of claim 17, wherein the method is used for one or more of the following: selectively targeting deep tissue of a subject, diagnosing and treating neuromuscular and psychiatric disorders, treating Parkinson's disease, ablation of deep tissue, pain control, nerve and muscle excitation, activation of immune and endocrine cells, electroporation, cardiac pacing, defibrillation, muscle training and rehabilitation, or deep brain stimulation.

23. A system, comprising:
a first electric pulse-delivering channel and a second electric pulse-delivering channel;
at least one pulse generator configured to produce at least a first bipolar electric pulse to be delivered from at least the first electric pulse-delivering channel and at least a second bipolar electric pulse to be delivered from at least the second electric pulse-delivering channel,
wherein the system is configured to superpose the at least the first bipolar electric pulse and the at least the second bipolar electric pulse to create a monopolar electric pulse at a location remote from the first and second channels; and,
at least one power supply operably connected to the at least one pulse generator.

24. The system of claim 23, wherein the at least the first electric pulse-delivering channel comprises tungsten rods.

25. The system of claim 23, wherein the at least the first electric pulse-delivering channel and the at least the second electric pulse-delivering channels comprises active electrodes.

26. The system of claim 25, wherein the active electrodes comprise needle electrodes.

27. The system of claim 25, wherein the active electrodes comprise stainless steel electrodes.

28. The system of claim 25, wherein the active electrodes are aligned in a linear array.

29. The system of claim 23, wherein either one or both of the first bipolar electric pulse and the second bipolar electric pulse comprises damped electric pulses.

30. The system of claim 23, wherein the first bipolar electric pulse and/or the second bipolar electric pulse is a sinusoidal pulse, a rectangular pulse, or a trapezoidal pulse.

31. The system of claim 23, wherein the at least one pulse generator is a multiphasic pulse generator.

32. The system of claim 23, wherein the first bipolar electric pulse or the second bipolar electric pulse comprises a biphasic or triphasic pulse and each phase of the biphasic or the triphasic pulse has different amplitude.

* * * * *